US010321905B2

(12) United States Patent
Martin et al.

(10) Patent No.: US 10,321,905 B2
(45) Date of Patent: Jun. 18, 2019

(54) SUTURING INSTRUMENT WITH JAW HAVING INTEGRAL NEEDLE COVER

(71) Applicant: Ethicon Endo-Surgery, LLC, Guaynabo, PR (US)

(72) Inventors: David T. Martin, Milford, OH (US); Chester O. Baxter, III, Loveland, OH (US); Mark J. Bookbinder, Blue Ash, OH (US); Daniel J. Mumaw, Liberty Township, OH (US); Andrew C. Deck, Dayton, OH (US); Frederick E. Shelton, IV, Hillsboro, OH (US); J. Bernar Ogzewalla, Maysville, KY (US)

(73) Assignee: Ethicon LLC, Guaynabo, PR (US)

( * ) Notice: Subject to any disclaimer, the term of this patent is extended or adjusted under 35 U.S.C. 154(b) by 145 days.

(21) Appl. No.: 14/918,802

(22) Filed: Oct. 21, 2015

(65) Prior Publication Data
US 2017/0112487 A1  Apr. 27, 2017

(51) Int. Cl.
*A61B 17/04* (2006.01)
*A61B 17/00* (2006.01)

(52) U.S. Cl.
CPC ...... *A61B 17/0469* (2013.01); *A61B 2017/00367* (2013.01)

(58) Field of Classification Search
CPC ........... A61B 17/0469; A61B 17/105; A61B 2017/00367; A61B 17/0493; A61B 17/04; A61B 17/06; A61B 17/06114
USPC ...................................................... 606/145
See application file for complete search history.

(56) References Cited

U.S. PATENT DOCUMENTS

| 5,308,353 | A | * | 5/1994 | Beurrier | A61B 17/0469 |
| | | | | | 112/169 |
| 8,702,732 | B2 | | 4/2014 | Woodard et al. | |
| 9,168,037 | B2 | | 10/2015 | Woodard et al. | |
| 9,357,998 | B2 | | 6/2016 | Martin et al. | |
| 9,375,212 | B2 | | 6/2016 | Martin et al. | |
| 9,474,522 | B2 | | 10/2016 | Deck et al. | |
| 2004/0260314 | A1 | * | 12/2004 | Lizardi | A61B 17/0469 |
| | | | | | 606/144 |

(Continued)

OTHER PUBLICATIONS

U.S. Appl. No. 14/917,841.
U.S. Appl. No. 14/918,841, filed Oct. 21, 2015.
U.S. Appl. No. 14/918,841.

*Primary Examiner* — Juie A Szpira
(74) *Attorney, Agent, or Firm* — Frost Brown Todd LLC

(57) ABSTRACT

A surgical instrument includes a body, a shaft, and a cartridge receiving assembly. The body has an actuator. The cartridge receiving assembly includes a first jaw and a second jaw. The first jaw is movable relative to the second jaw between an open position and a closed position. The first and second jaws are configured to receive a suture cartridge therebetween when the first jaw is in the open position. The first and second jaws are configured to secure a suture cartridge therebetween and thereby operatively couple the actuator with the suture cartridge when the first jaw is in the closed position. The first jaw is further configured to receive a needle of the suture cartridge directly thereagainst when the first jaw is in the closed position such that the first jaw is configured to capture the needle within the suture cartridge.

20 Claims, 19 Drawing Sheets

(56) References Cited

U.S. PATENT DOCUMENTS

| | | | |
|---|---|---|---|
| 2010/0078335 A1* | 4/2010 | Iyengar | G01N 27/3273 |
| | | | 205/782 |
| 2010/0152751 A1* | 6/2010 | Meade | A61B 17/0469 |
| | | | 606/144 |
| 2012/0217184 A1* | 8/2012 | Edwards | A61M 5/2033 |
| | | | 206/571 |
| 2015/0133967 A1 | 5/2015 | Martin | |
| 2015/0142018 A1* | 5/2015 | Sniffin | A61B 17/06066 |
| | | | 606/144 |
| 2016/0367240 A1 | 12/2016 | Shelton, IV et al. | |
| 2016/0367243 A1 | 12/2016 | Martin et al. | |

* cited by examiner

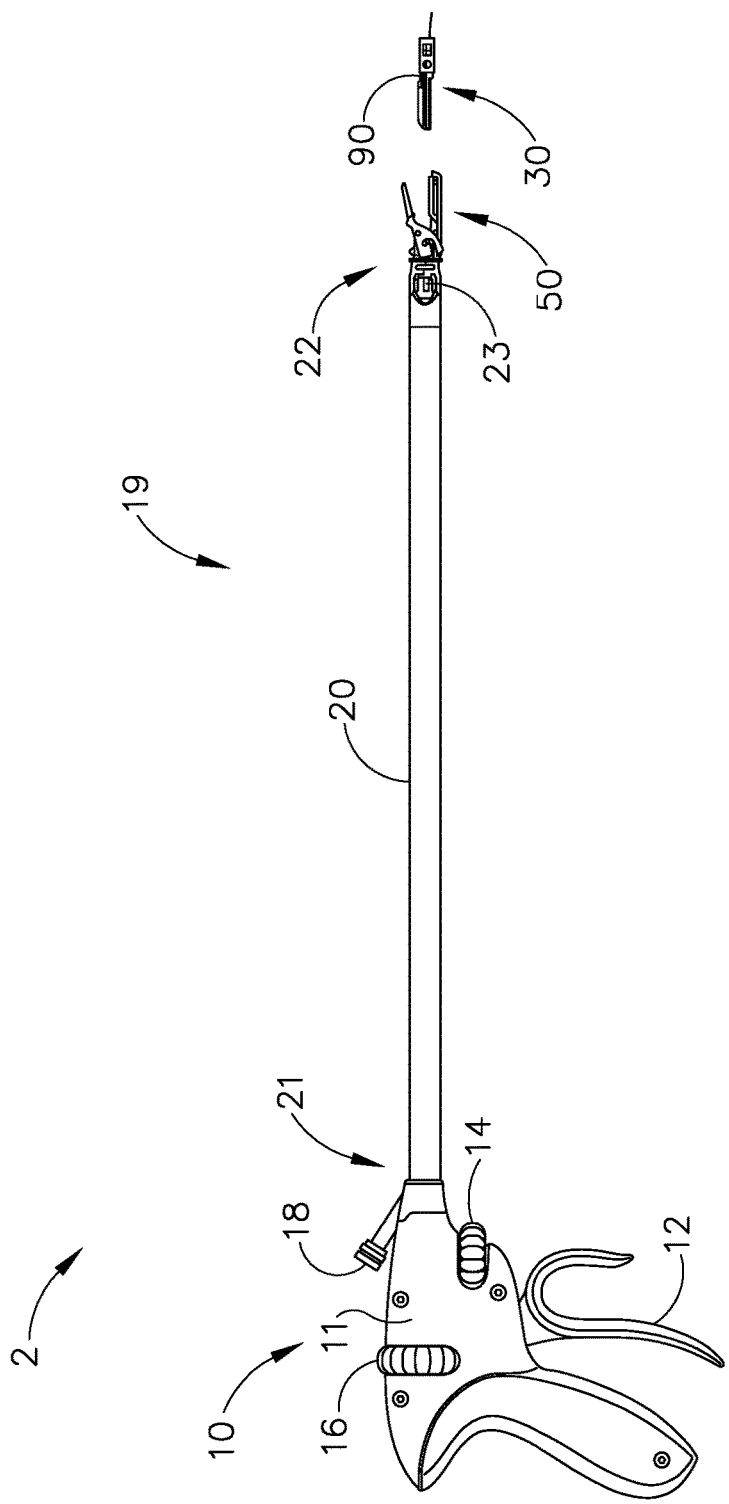

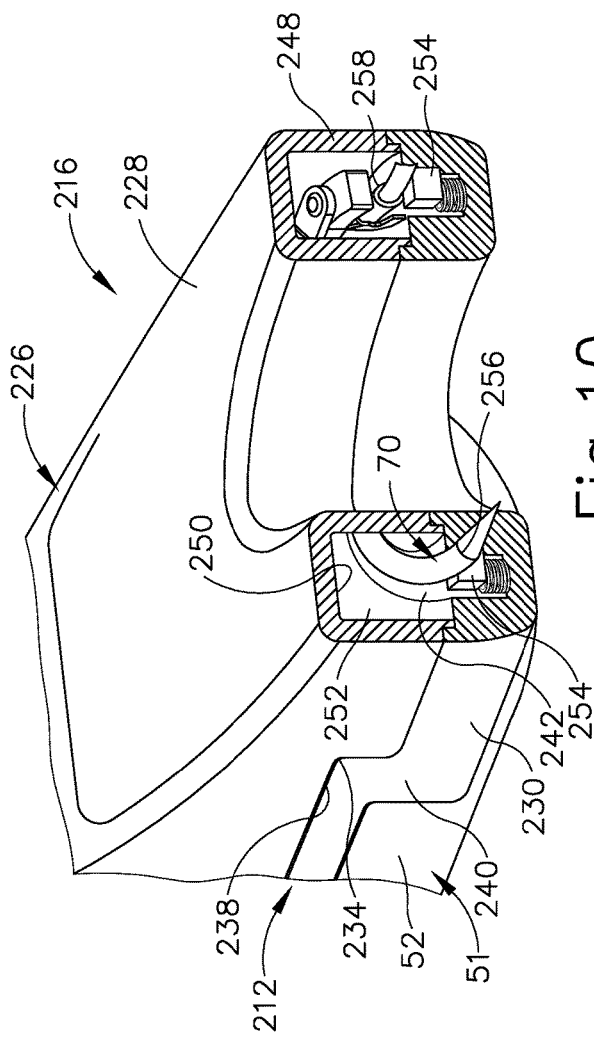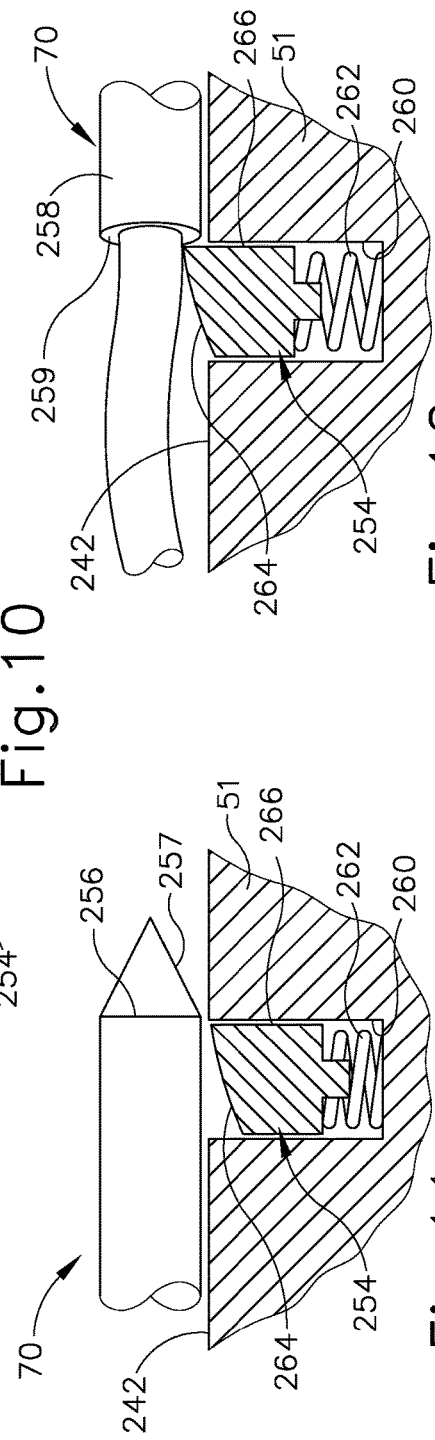

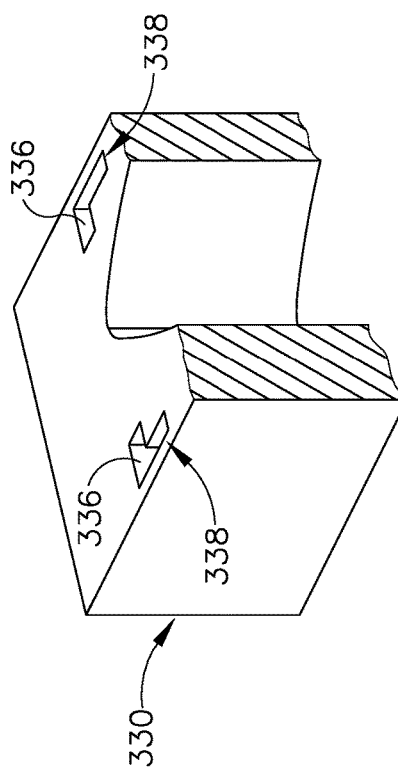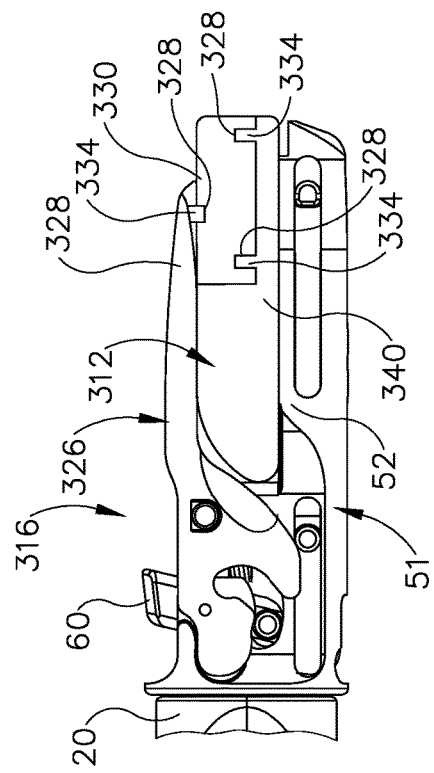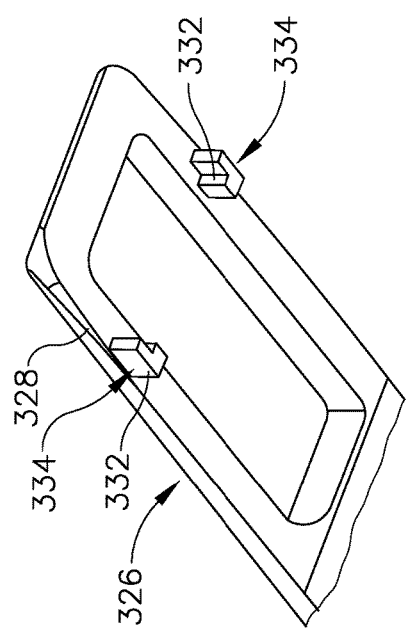

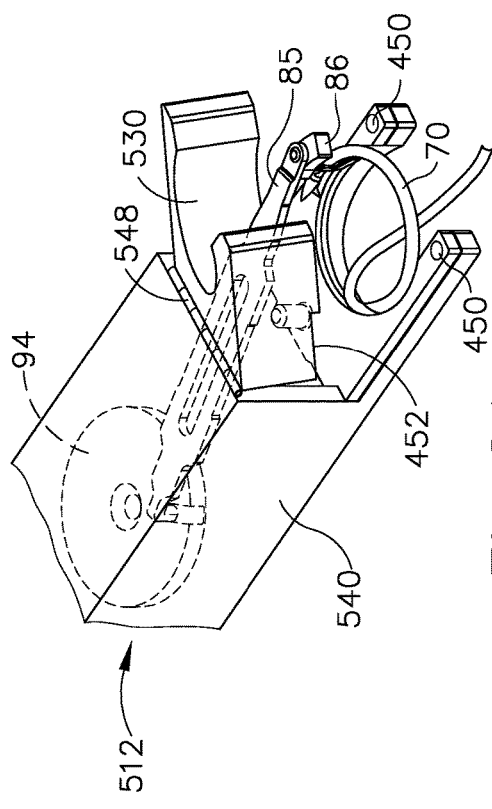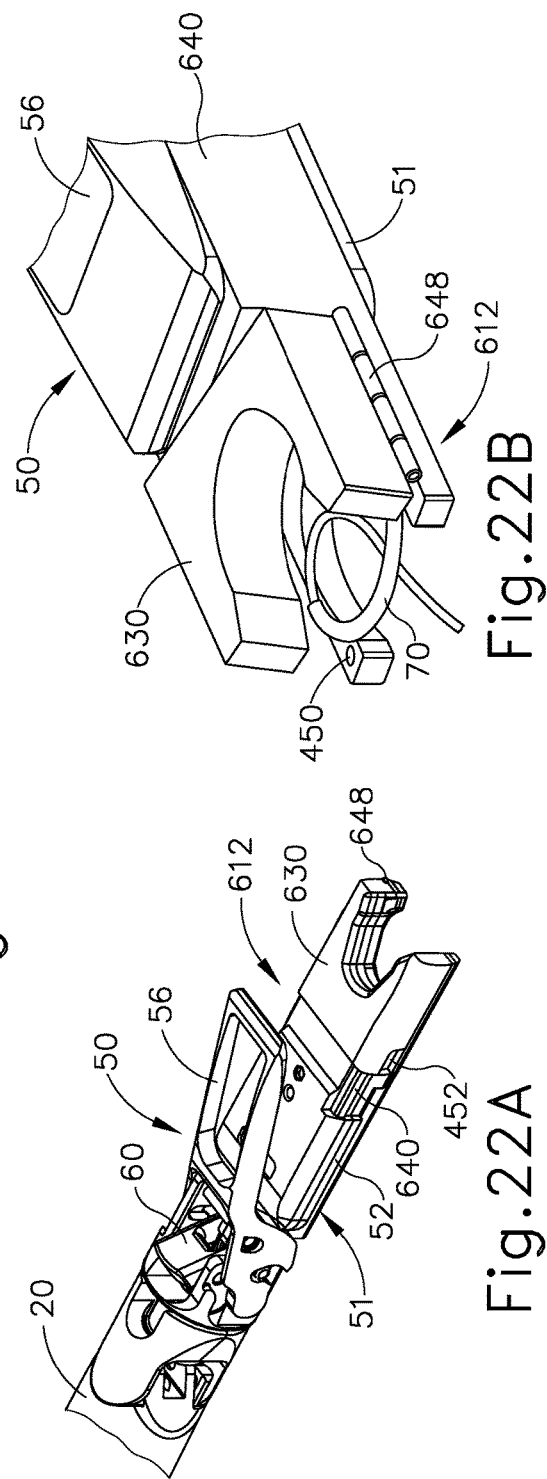

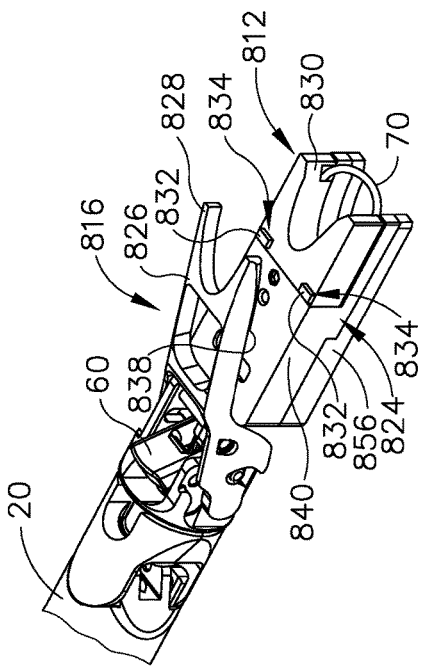
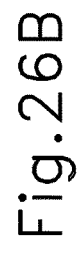
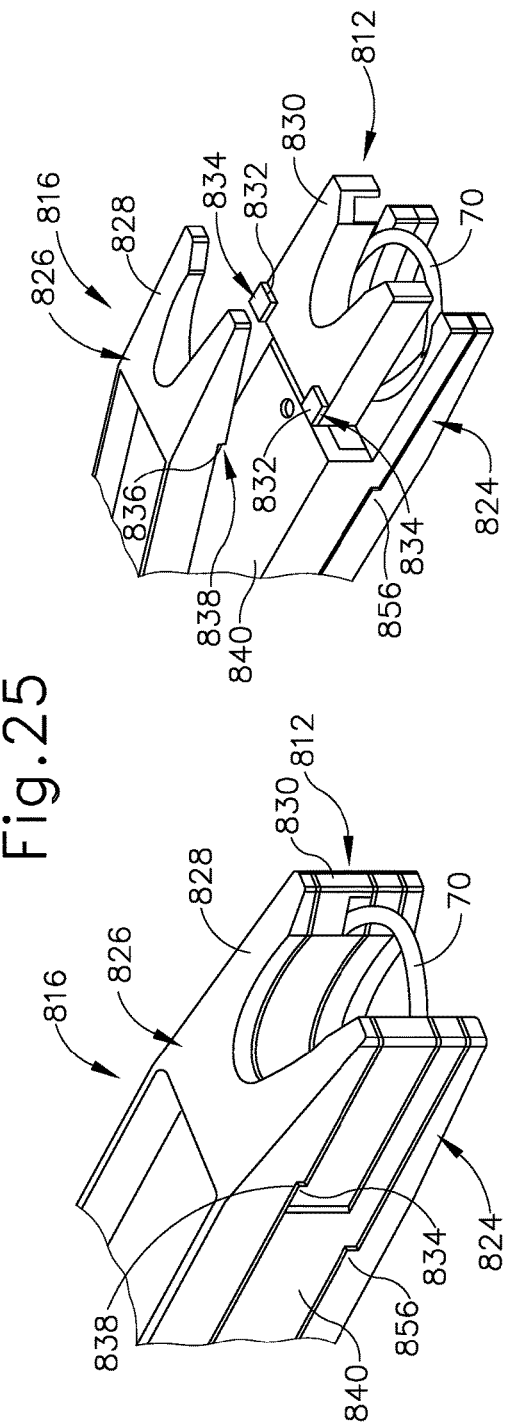

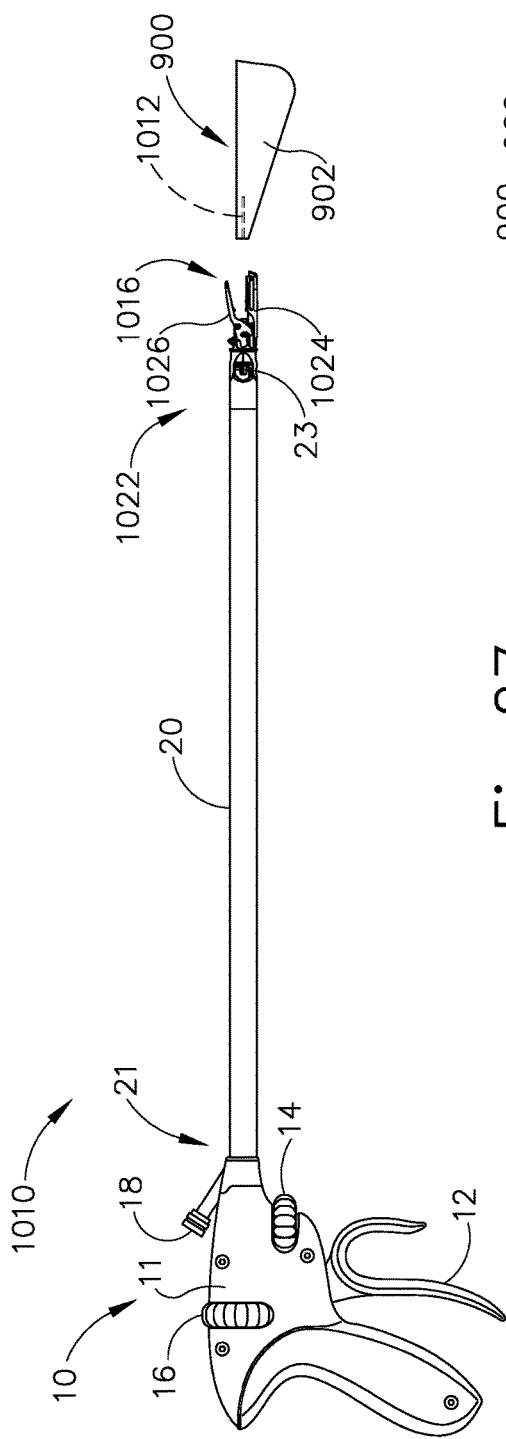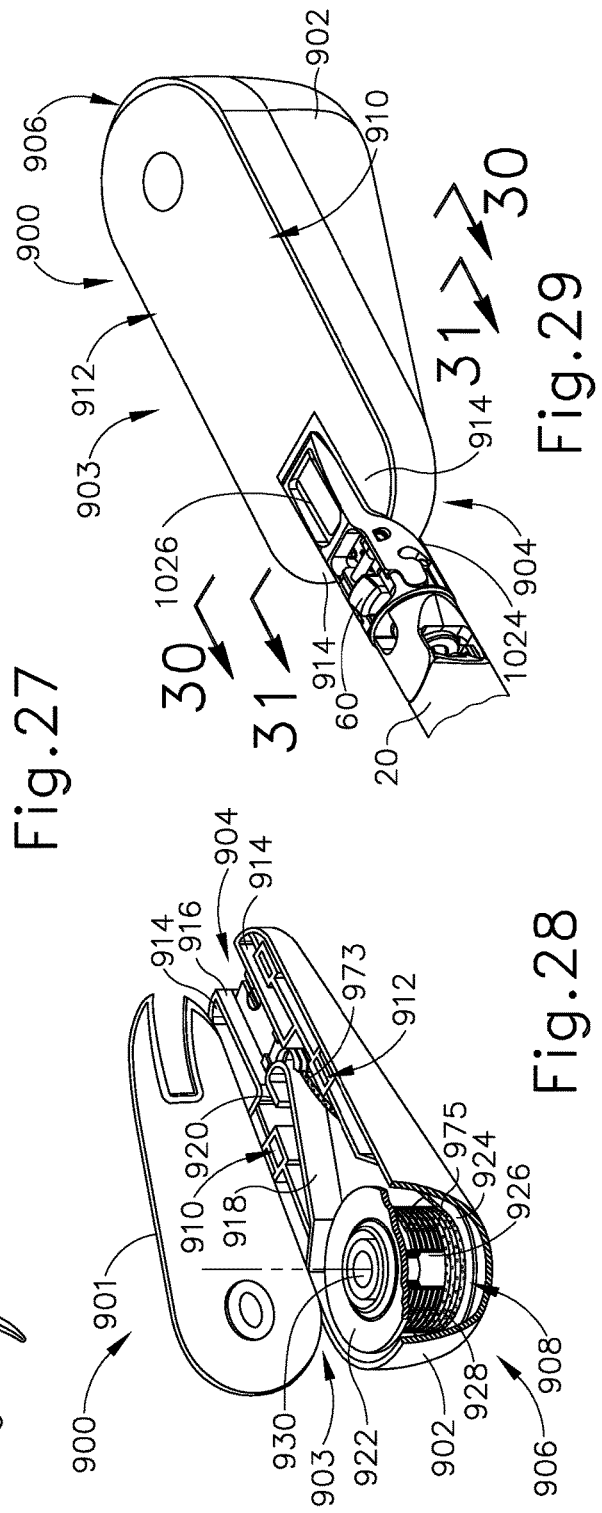

SUTURING INSTRUMENT WITH JAW HAVING INTEGRAL NEEDLE COVER

BACKGROUND

Sutures may be used in a wide variety of surgical procedures. Manual suturing may be accomplished by the surgeon using a fine pair of graspers to grab and hold a suture needle, pierce the tissue with the needle, let go of the needle, and re-grasp the needle to pull the needle and accompanying suture thread through the tissues to be sutured. Such needles may be curved with the suture attached to the trailing end of the needle.

Some surgical instruments automate at least part of the suturing procedure. Examples of automated suturing instruments are described in U.S. Pat. No. 8,702,732, entitled "Laparoscopic Suturing Instrument with Dual-Action Needle Graspers," issued Apr. 22, 2014, the disclosure of which is incorporated by reference herein; U.S. Pub. No. 2011/0313433, entitled "Laproscopic Suture Device with Asynchronous In-Line Needle Movement," published Dec. 22, 2011, issued as U.S. Pat. No. 9,168,037 on Oct. 27, 2015, the disclosure of which is incorporated by reference herein; U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; and U.S. patent application Ser. No. 14/297,993, entitled "Jawed Cartridge Receiving Assembly for Needle Cartridge," filed Jun. 6, 2014, issued as U.S. Pat. No. 9,474,522 on Oct. 25, 2016, the disclosure of which is incorporated by reference herein.

While various kinds of suturing instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 1 depicts a side view of a first exemplary surgical suturing instrument having a first exemplary cartridge receiving assembly;

FIG. 10 depicts a cross-sectional perspective view of the cartridge and the cartridge receiving assembly of FIG. 7, taken along section line 10-10 of FIG. 9;

FIG. 11 depicts a side cross-sectional view of a leading end portion of a needle within the cartridge of FIG. 7;

FIG. 12 depicts a side cross-sectional view of a trailing end portion of a needle within the cartridge of FIG. 7;

FIG. 16 depicts an enlarged upper perspective view of an engagement region of the cartridge of FIG. 14;

FIG. 17 depicts an enlarged lower perspective view of an engagement region of the cartridge receiving assembly of FIG. 14;

FIG. 18 depicts an enlarged side view of the cartridge and the cartridge receiving assembly of FIG. 14, with the cartridge receiving assembly in a closed position;

FIG. 21 depicts an enlarged perspective view of a still another exemplary cartridge with a needle cover hingedly attached to a remainder of the cartridge by a living hinge;

FIG. 22A depicts an enlarged right perspective view of a another exemplary cartridge and the cartridge receiving assembly of FIG. 1 in the open position;

FIG. 22B depicts an enlarged left perspective view of the cartridge and the cartridge receiving assembly of FIG. 22A in a closed position, with a needle cover hingedly attached to a remainder of the cartridge by an integral strap hinge;

Figure 23:
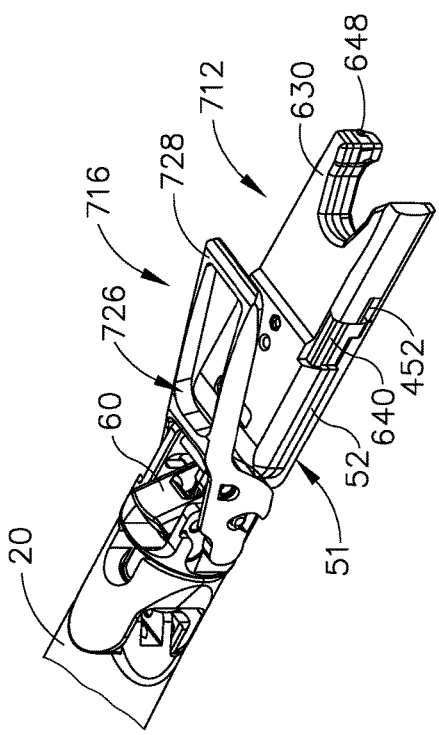
Figure 24B:
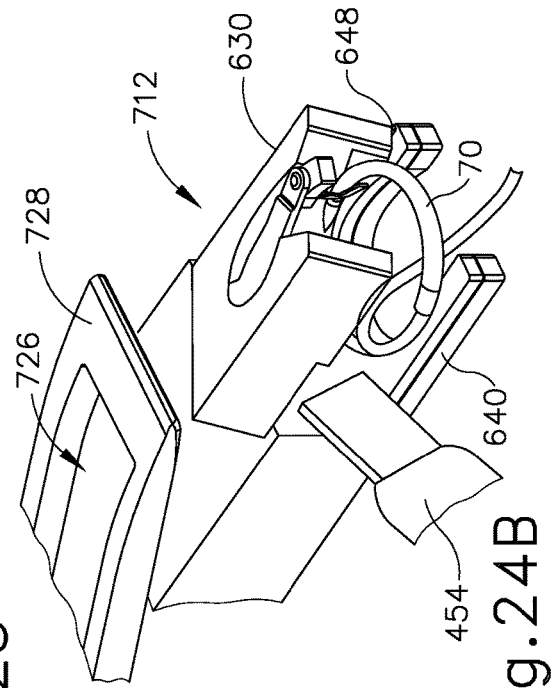
Figure 24A:
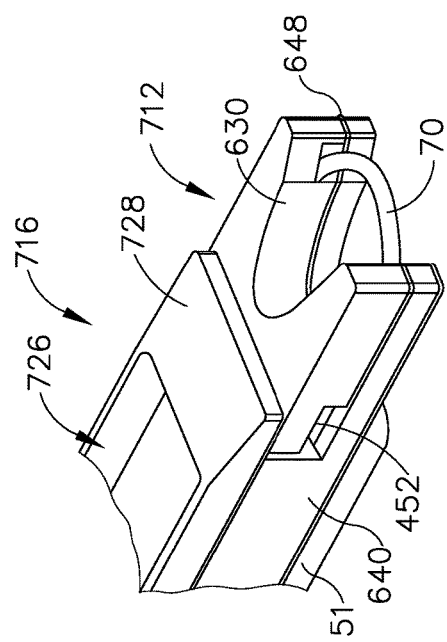
Figure 30:
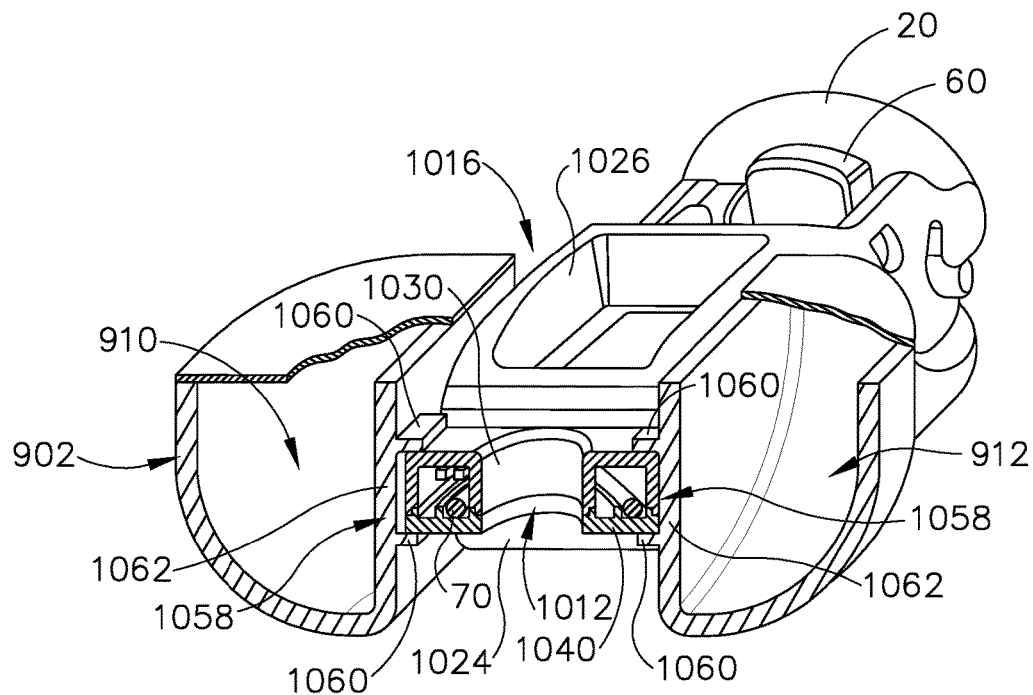
Figure 31:
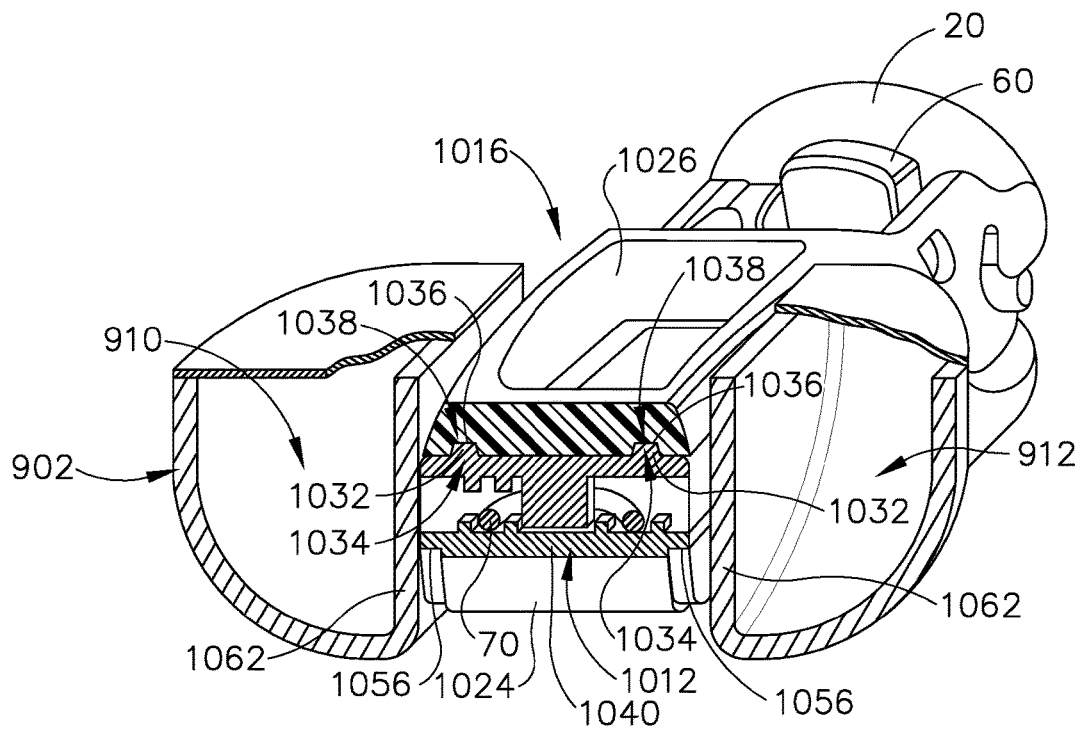

FIG. 23 depicts an enlarged perspective view of another exemplary cartridge and another exemplary cartridge receiving assembly, with the cartridge receiving assembly in an open position;

FIG. 24A depicts an enlarged perspective view of the cartridge and the cartridge receiving assembly of FIG. 23, with the cartridge receiving assembly in a closed position;

FIG. 24B depicts an enlarged perspective view of the cartridge and the cartridge receiving assembly of FIG. 23, with the cartridge receiving assembly in the open position and the needle cover hingedly attached to the remainder thereof by the integral strap hinge;

FIG. 25 depicts an enlarged perspective view of an another exemplary cartridge and another exemplary cartridge receiving assembly, with the cartridge receiving assembly in an open position;

FIG. 26A depicts an enlarged perspective view of the cartridge and the cartridge receiving assembly of FIG. 25, with the cartridge receiving assembly in a closed position;

FIG. 26B depicts an enlarged perspective view of the cartridge and the cartridge receiving assembly of FIG. 25, with the cartridge receiving assembly in the open position and the needle cover being removed therefrom;

FIG. 27 depicts a side view of another exemplary surgical suturing instrument having another exemplary cartridge and another exemplary cartridge receiving assembly in an exemplary packaging;

FIG. 28 depicts a perspective view of the packaging of FIG. 27, with a lid of the packaging in an open position;

FIG. 29 depicts an enlarged rear perspective view of the cartridge receiving assembly of FIG. 27 engaging the cartridge of FIG. 27 while the cartridge is disposed in the packaging of FIG. 27;

FIG. 30 depicts a perspective cross-sectional view of the cartridge receiving assembly of FIG. 27 engaging the cartridge of FIG. 27 while the cartridge is disposed in the packaging of FIG. 27, taken along line 30-30 of FIG. 29; and FIG. 31 depicts a perspective cross-sectional view of the cartridge receiving assembly of FIG. 27 engaging the cartridge of FIG. 27 while the cartridge is disposed in the packaging of FIG. 27, taken along line 31-31 of FIG. 29.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

For clarity of disclosure, the terms "proximal", "distal", "upper", and "lower" are defined herein relative to an operator or other operator grasping a surgical instrument having a distal surgical end effector. The term "proximal" refers the position of an element closer to the operator or other operator, and the term "distal" refers to the position of an element closer to the surgical end effector of the surgical instrument and further away from the operator or other operator. The term "upper" refers to the position of the element closer to a top of the surgical instrument when viewed by the operator from above, and the term "lower" refers to the position of the element closer to a bottom of the surgical instrument when viewed by the operator from below. As such, proximal and distal portions are generally in longitudinal opposition as described herein, whereas upper and lower portions are generally in transverse opposition as described herein.

I. Overview of Exemplary Surgical Suturing Instrument

FIG. 1 illustrates an example of a surgical suturing instrument (2). Instrument (2) comprises a handle assembly (10) and a shaft assembly (19) having an elongate shaft (20) extending from a distal end portion (22) to a proximal end portion (21) thereof. Distal end portion (22) includes a cartridge receiving assembly (50), which is operable to receive a needle applier cartridge (30). Shaft (20) defines a longitudinal axis extending from proximal end portion (21) to distal end portion (22). Handle assembly (10) is connected to proximal end portion (21) of shaft (20). In this example handle assembly (10) is a manual pistol grip handle. However, a variety of other manual actuators could also be used, including but not limited to a scissor grip handle, a syringe grip handle, endoscopic rotary knobs, and the like. Handle assembly (10) could also take the form of a robotic interface, such as a DAVINCI puck, or a housing comprising gears or pulleys, servomechanisms, and the like.

Needle applier cartridge (30) is connected to distal end portion (22) of shaft (20) via cartridge receiving assembly (50). Needle applier cartridge (30) is operable to rotate an arced needle in a circular path enabling a surgeon to selectively apply sutures. In some alternative versions, needle applier cartridge (30) is integral with shaft (20) and handle assembly (10) as a unitary disposable instrument intended for a single surgical procedure. Needle applier cartridge (30) may also be integral with shaft (20) and handle assembly (10) as a reusable instrument. Optionally, as illustrated here, needle applier cartridge (30) may be provided in a disposable cartridge body (90) and shaft (20) includes cartridge receiving assembly (50) to releasably hold cartridge body (90). In some such versions, shaft (20) and handle assembly (10) may also be disposable or reusable. Versions with reusable components are intended to be cleaned, sterilized, and reused for a multiple surgical procedures, and may include a flush port (18) to facilitate cleaning. The preferable life cycle of a reusable instrument is at least 50 operations, more preferably at least 150 operations, and most preferably at least 200 operations. Reusable components may be built using materials that can withstand autoclave sterilization temperatures of at least 135 degrees Celsius, although low temperature materials can also be used with low temperature sterilization techniques known in the art.

A first user input member (12), shown here as a trigger that pivots between opened and closed positions, may be used to selectively actuate needle applier cartridge (30). The trigger may be spring biased to return the trigger to its open position. A second user input member (14), shown here as a rotary knob, may be used to selectively articulate shaft (20). A third user input member (16), shown here as a rotary knob, may be used to selectively rotate needle applier cartridge (30) about shaft (20). Of course, the number, type, configuration, and operation of input members (12, 14, 16) may vary.

Shaft (20) includes an articulation joint (23). Rotary knob (14) is operable to selectively articulate joint (23) via a joint drive assembly (118). Rotary knob (14) rotates in a plane spaced below and generally parallel with shaft (20). An axle (121) connects rotary knob (14) to a disk (not shown) in housing (11) that also rotates in a plane generally parallel with the shaft (20) for position distal end portion (22) of shaft assembly (19) relative to proximal end portion (21).

Figure 2A:
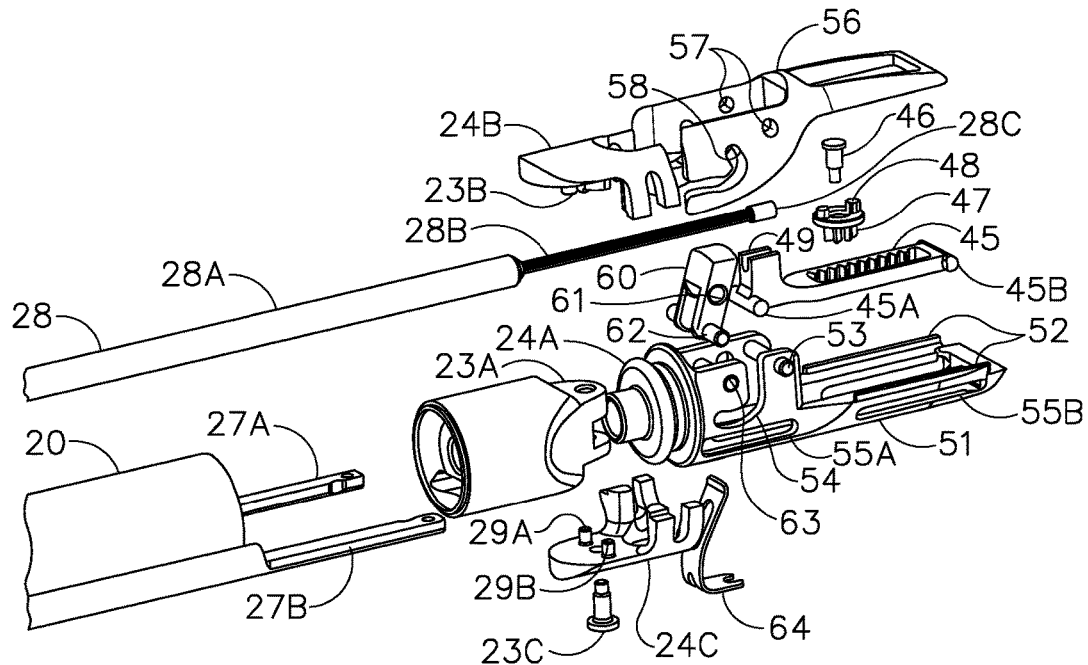
FIG. 2A depicts a top perspective exploded view of the cartridge receiving assembly of the instrument of FIG. 1.
Figure 2B:
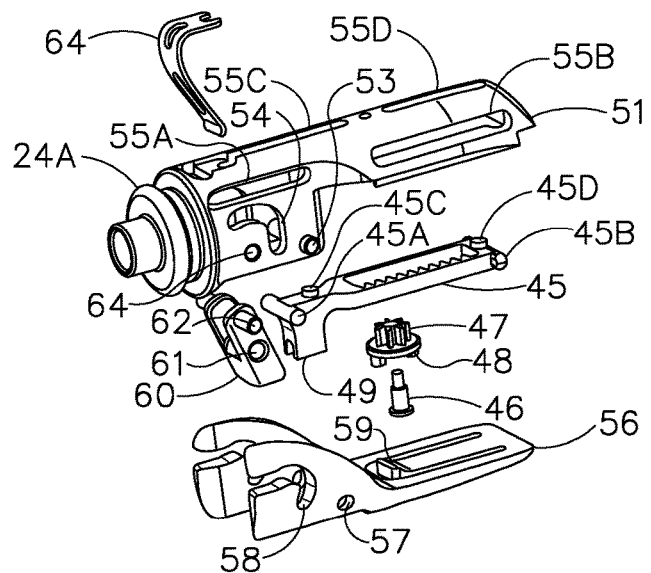
FIG. 2B depicts a bottom perspective exploded view of the cartridge receiving assembly of FIG. 2A.

FIGS. 2A-2B illustrate exploded views of cartridge receiving assembly (50) of the present example. Distal end portion (22) of shaft (20) comprises articulation joint (23) and a rotational bearing (24). Articulation joint (23) includes a knuckle (23A) that receives pins (23B, 23C), which are connected to bearing supports (24B, 23C). Thus, pins (23B, 2C) define the pivoting axis for articulation joint (23), enabling cartridge receiving assembly (50) to articulate left and right relative the shaft (20), away from the longitudinal axis defined by shaft (20). Rods (27A, 27B) are operably connected to articulation joint (23). In this example, rods (27A, 27B) extend through shaft (20), through knuckle (23A), and connect to pins (29A, 29B) on bearing support (24C). Rods (27A, 27B) are operatively connected to rotary knob (14) to opposingly push and pull rods (27A, 27B). In other words, rotary knob (14) is operable to drive rods (27A, 27B) at the same time in opposite longitudinal directions, such that rod (27A) will translate distally while rod (27B) translates proximally; and such that rod (27B) will translate distally while rod (27A) translates proximally. Because pins (29A, 29B) are laterally spaced from the pivoting axis, the simultaneous push and pull action will in turn articulate cartridge receiving assembly (50) about joint (23) relative to shaft (20).

Rotational bearing (24) is positioned distal to articulation joint (23). Bearing (24) includes a circumferential flange (24A) that is captured between the bearing supports (24B, 24C) such that the flange (24A) can rotate relative the bearing supports (24B, 24C) and enabling unbounded rotation of cartridge receiving assembly (50) relative shaft (20) about the longitudinal axis defined by shaft (20). A drive rod (28) extends through shaft (20). In this example, drive rod (28) comprises a proximal rigid portion (28A) and a distal bendable portion (28B) that are fixedly connected to one another. Bendable portion (28B) extends through articulation joint (23) and through bearing (24); distal end (28C) is fixedly connected to a mount (49) on a rack (45).

Rack (45) reciprocates longitudinally in lower jaw (51) with followers (45A, 45B, 45C, 45D) constrained in tracks (55A, 55B, 55C, 55D), respectively. Tracks (55A, 55B, 55C, 55D) open through lower jaw (51), providing fluid passages to the internal components within the lower jaw (51), thus facilitating easier cleaning. A pinion (47) is mounted to lower jaw (51) by a pin (46) in the rack (45) such that longitudinal reciprocation of the rack (45) is converted into rotational reciprocation of pinion (47). A key (48) communicates the reciprocating rotation to a rotary input (94) in cartridge body (90), which in turn actuates needle applier cartridge (30).

Drive rod (28) is operatively connected to first user input member (12) and to third user input member (16). Actuation of first user input member (12) will impart axial push and pull loads on drive rod (28) to longitudinally reciprocate rack (45) and thereby actuate needle applier cartridge (30). Actuation of third user input member (16) will impart a rotational load on drive rod (28) thus rotating cartridge receiving assembly (50) about bearing (24) relative to shaft (20). Accordingly, a single drive rod (28) operates to both actuate needle applier cartridge (30) as well as control distal rotation of needle applier cartridge (30) about the longitudinal axis of shaft (20). By consolidating dual functions with a single drive rod (28), the number of components is reduced, and more space is provided in the shaft (20), which may make the device less expensive to manufacture and easier to clean.

Cartridge receiving assembly (50) is dimensioned and adapted to receive and hold cartridge body (90). As shown in FIGS. 2A-2B, cartridge receiving assembly (50) of this example has upper and lower jaws (56, 51) that are operable to transition between an open configuration and a closed configuration. In the closed configuration, jaws (56, 51) are operable to receive and retain cartridge body (90). In the closed configuration, jaws (56, 51) are operable to release cartridge body (90). In the present example, lower jaw (51) is stationary and upper jaw (56) pivots. Alternatively, the arrangement could be reversed, or in some versions both jaws (56, 51) could pivot. Lower jaw (51) has two laterally offset longitudinal rails (52) that are dimensioned and adapted to receive cartridge body (90). Rails (52) help longitudinally align cartridge body (90) in cartridge receiving assembly (50) and laterally retain cartridge body (90) in jaws (51, 56). Upper jaw (56) pivots relative lower jaw (51) about a pin (53) that is received in holes (57). A tooth (59) is resiliently oriented downwardly from upper jaw (56) toward lower jaw (51) with a ramped distal face and a stepped proximal face. Tooth (59) is dimensioned and adapted to latch with cartridge body (90) and longitudinally retain cartridge body (90) in jaws (51, 56). Tooth (59) deflects by virtue of a resilient cantilevered arm extending proximally from the distal end of upper jaw (56). In this example, tooth (59) and the cantilevered arm are monolithic with upper jaw (56), thus reducing the number of components and moving pieces, which may make the device less expensive to manufacture and easier to clean.

A button (60) is operable to open and close jaws (51, 56). While button (60) could be placed on or near the handle assembly (10) in some versions, in this example button (60) is positioned adjacent cartridge receiving assembly (50), which eliminates a linkage in shaft (20) thus creating space in shaft (20) and making the device less expensive and easier to clean. The action of button (60) may vary, but in this example button (60) pivots relative to lower jaw (51) about a pin (63) that is received in hole (61). A follower (62) is received by cam slots (54, 58). Pivoting button (60) proximally will open jaws (51, 56), while pivoting button (60) distally will close jaws (51, 56). A spring (64) engages and biases button (60) distally. By pulling button (60) proximally, follower (62) will drive cam slot (58) to open upper jaw (56). When button (60) is released, spring (64) will resiliently drive button (60) distally to close upper jaw (56).

Figure 3A:
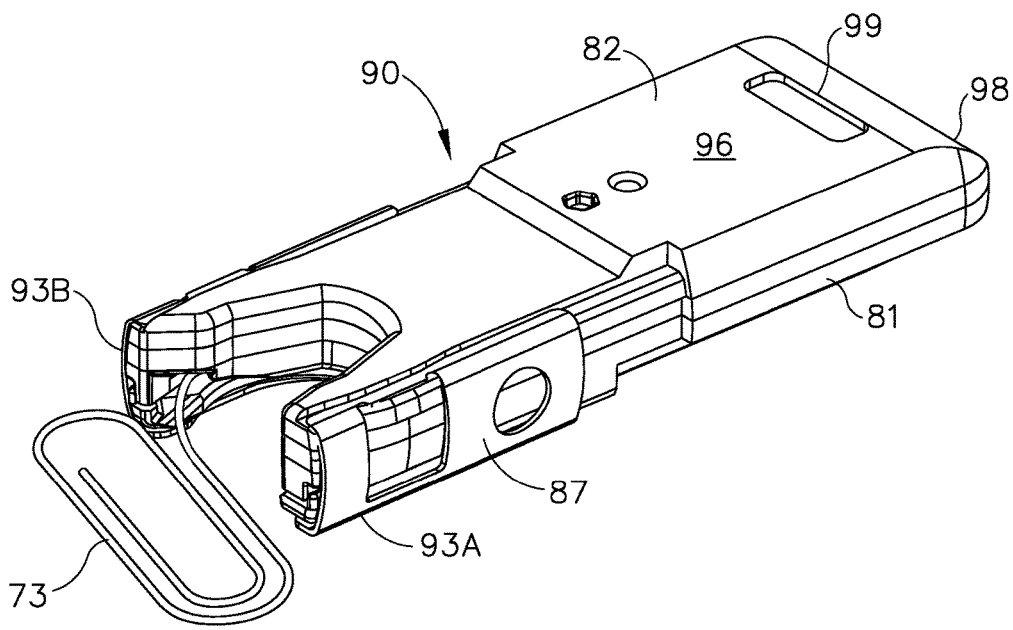
FIG. 3A depicts a top perspective view of a first exemplary cartridge configured for receipt in the cartridge receiving assembly of FIG. 2A.
Figure 3B:
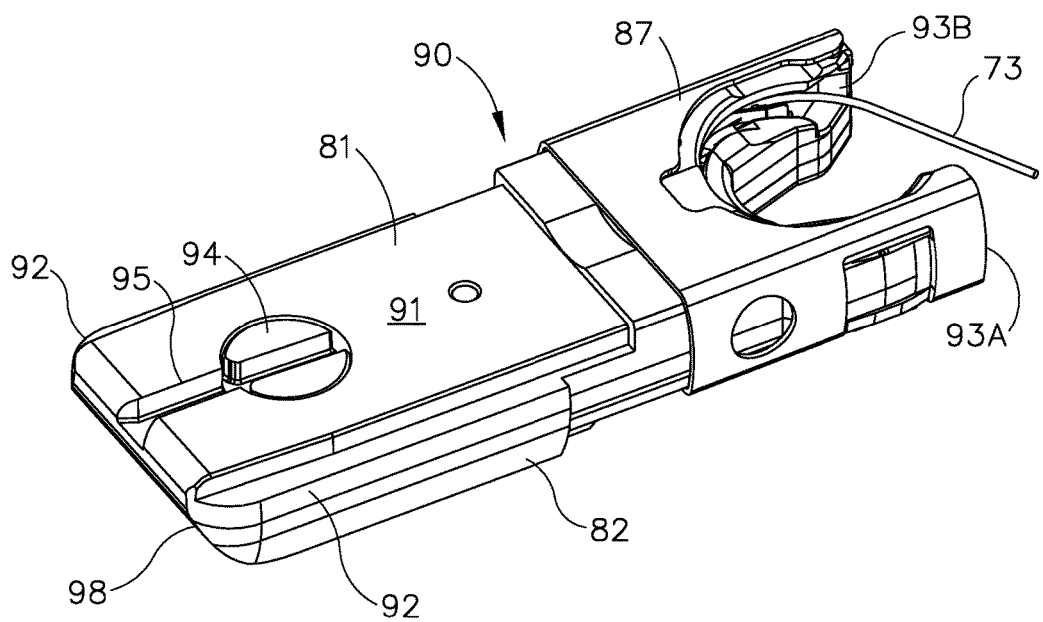
FIG. 3B depicts a bottom perspective view of the cartridge of FIG. 3A.

FIGS. 3A-3B illustrate cartridge body (90) of the present example in greater detail. A lower face (91) of cartridge body (90) is adapted to engage lower jaw (51); and an upper face (96) is adapted to engage upper jaw (56). Poke-yoke features on cartridge body (90) prevent improper insertion of cartridge body (90) into cartridge receiving assembly (50), but also contribute to the aesthetic appearance of cartridge body (90). For instance, lower face (91) has a pair of longitudinal notched shoulders (92) that are dimensioned to interface and mate with rails (52). In this example, notched shoulders (92) are shaped as a stepped rabbet, but a variety of other aesthetic shapes could also be employed such as chamfers and radii. In contrast, upper face (96) is asymmetrical relative lower face (91) and lacks shoulder notches, so upper face (96) would interfere with rails (52) if cartridge body (90) were inserted upside-down in cartridge receiving assembly (50). In another instance, the geometry of a proximal face (98) of cartridge body (90) is vertically asymmetrical and thus prevents cartridge body (90) from being inserted upside-down between jaws (51, 56). In this example, proximal face (98) comprises a curved surface that gently transitions to upper face (96), which matches similar geometry in cartridge receiving assembly (50); while the transition to lower face (91) has a tighter radius. Of course, a variety of other asymmetrical aesthetic geometries could also be employed that could contribute to the visual appearance and/or poke-yoke aspects of cartridge body (90).

Arms (93A, 93B) define a generally U-shaped distal end on cartridge body (90). A slot (95) and rotary input (94) are aligned and dimensioned to receive the key (48) while cartridge body (90) is being slid into cartridge receiving assembly (50). When cartridge body (90) is fully seated into cartridge receiving assembly (50), a step (99) aligns with and receives tooth (59) to latch cartridge body (90) in cartridge receiving assembly (50). Key (48) also aligns with rotary input (94), thereby providing a torsional interface that rotationally couples pinion (47) and rotary input (94). In use, the needle (70) exits arm (93A) and enters arm (93B).

Figure 4:
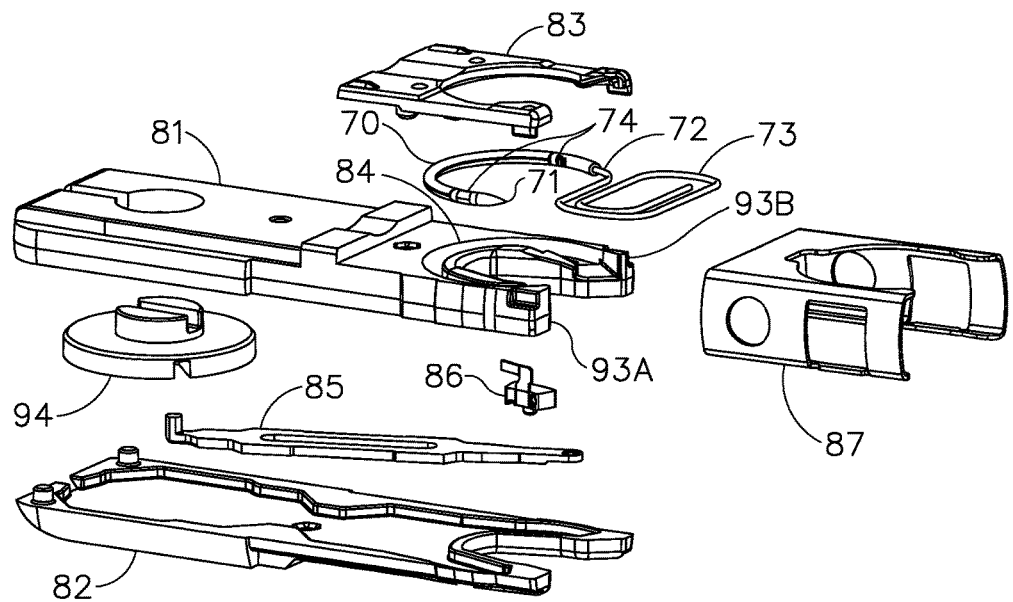
FIG. 4 depicts an exploded view of the cartridge of FIG. 3A.

As shown in FIGS. 3A-4, cartridge body (90) further comprises a lower body (81), an upper body (82), a needle (70), and a needle cover (83). Needle driver (86), rotary input (94), and a link (85) are captured between lower body (81) and upper body (82). Bodies (81, 82) may be attached to one another using a variety of known techniques, including welds, pins, adhesives, and the like to form cartridge body (90). Needle (70) has a leading end (71) and a length of suture (73) extending from a trailing end (72) thereof. Needle (70) orbits in a circular path defined by a needle track (84) and between arms (93A, 93B). Needle (70) includes notches (74) that are configured to facilitate engagement between needle driver (86) and needle (70). Needle (70) is captured in needle track (84) by needle cover (83). A cage (87) slides over bodies (81, 82) and needle cover (83) to attach needle cover (83) against lower body (81).

Figure 5A:
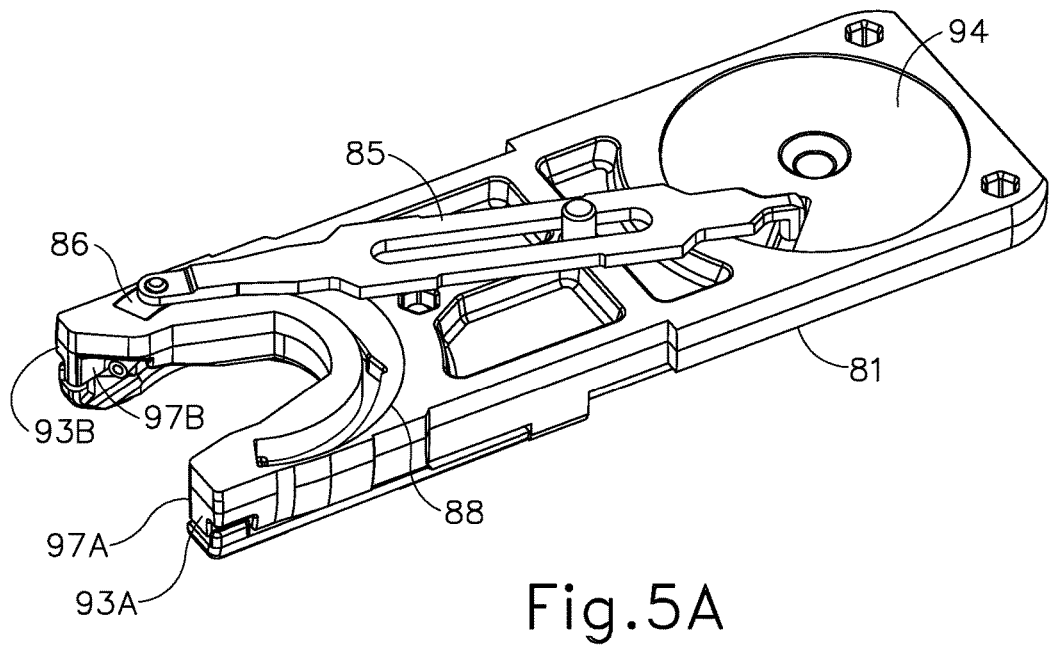
FIG. 5A depicts a perspective view of a drive assembly of the cartridge of FIG. 3A, with the drive assembly at one end of its stroke.
Figure 5B:
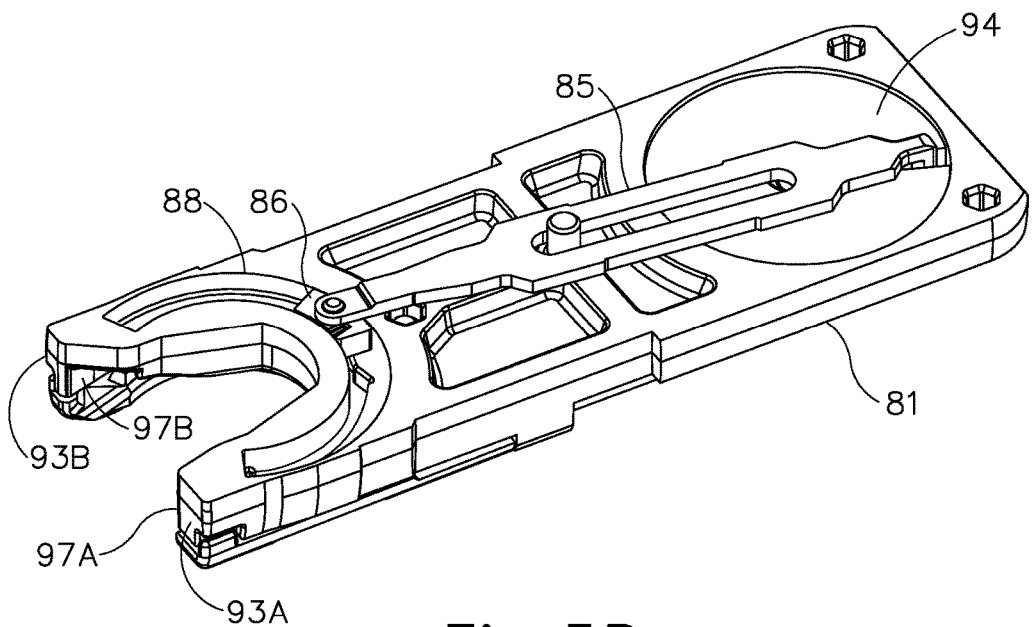
FIG. 5B depicts a perspective view of the drive assembly of FIG. 5A, with the drive assembly at mid-stroke.
Figure 5C:
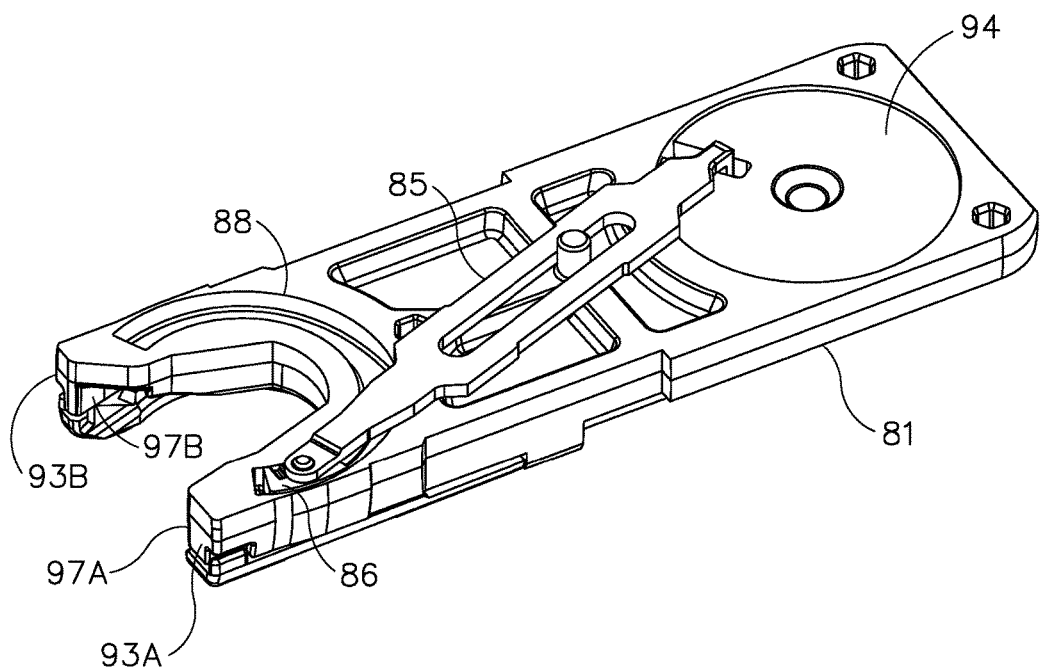
FIG. 5C depicts a perspective view of the drive assembly of FIG. 5A, with the drive assembly at the other end of its stroke.

FIGS. 5A-5C illustrate an example of a drive stroke of the transmission in cartridge body (90) for driving needle (70) in a circular, orbital path. However, it should be understood that needle (70) and suture (73) are omitted from FIGS. 5B-5C for clarity. Needle driver (86) rides in a carrier track (88) and extends into needle track (84) (see FIG. 4) to engage and drive needle (70). Link (85) connects rotary input (94) to needle driver (86). FIG. 5A shows needle driver (86) positioned at one end of its stroke in carrier track (88). As shown in FIG. 5B, counterclockwise rotation of rotary input (94) will translate needle driver (86) clockwise along carrier track (88), thereby driving needle (70) clockwise. As shown in FIG. 5C, continued counterclockwise rotation of the rotary input (94) will continue to translate needle driver (86) and thereby drive needle (70) clockwise until it reaches the other end of its stroke in carrier track (88). In this example, the drive stroke rotates the needle (70) in its circular path along an angular range of about 180 degrees. For the return stroke, the sequence can be reversed by rotating the rotary input (94) clockwise, which will translate needle driver (86) counterclockwise in carrier track (88). Needle driver (86) is disengaged from needle (70) during the return stroke until needle driver (86) reaches the end of the return stroke. Needle driver (86) will re-engage needle (86) upon completing the return stroke. Thus, a sequence of drive and return strokes will rotate the needle (70) in a circular path.

Figure 6:
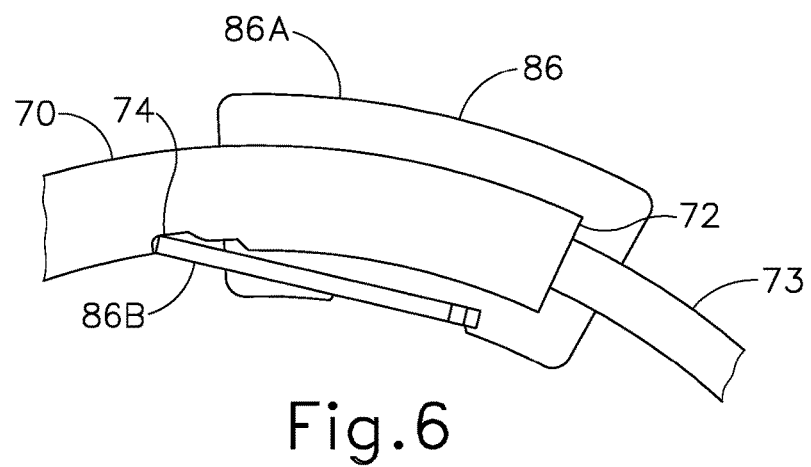
FIG. 6 depicts a partial plan view of a needle driver of the cartridge of FIG. 3A engaging a needle of the cartridge of FIG. 3A.

FIG. 6 illustrates a detailed view of needle driver (86) engaging needle (70). Needle driver (86) comprises a carrier (86A) and a driver (86B). Carrier (86A) is dimensioned to slideably fit in carrier track (88). Driver (86B) is attached to carrier (86A) and is operative to engage needle (70) at an oblique angle. Leftward movement of needle driver (86) will cause driver (86B) to engage proximal notch (74) of needle (70) during the drive stroke. When so engaged, needle (70) will slide in needle track (84) in unison with needle driver (86). Due to the oblique angle, rightward movement of needle driver (86) will disengage driver (86B) from proximal notch (74) of needle (70) and slide over the stationary needle (70) during the return stroke.

Referring back to FIGS. 5A-5C and FIG. 6, when first user input member (12) (see FIG. 1) is depressed, closing the trigger, needle driver (86) will be actuated through its drive stroke where it orbits along an angular range of motion at least about 180 degrees counterclockwise to a driven position as shown in FIG. 5C. During the drive stroke, driver (86B) engages proximal notch (74) and will in unison rotate needle (70) about 180 degrees along an orbital path to its extended position. Needle (70) will span across arms (93A, 93B) between exit port (97A) and entrance port (97B). Tissue interposed between arms (93A, 93B) will be pierced by leading end (71) of needle (70).

When first user input member (12) (see FIG. 1) is released and the spring return opens the trigger, needle driver (86) reciprocates through its return stroke where it orbits along an angular range of motion about 180 degrees clockwise back to the return position shown in FIG. 5A. During the return stroke, driver (86B) slides over the needle (70). Driver (86B) is then adjacent the distal notch (74). When first user input member (12) is depressed again closing the trigger, needle driver (86) will again be actuated through its drive stroke where it orbits along an angular range of motion about 180 degrees counterclockwise to the driven position as shown in FIG. 5C. During the drive stroke, driver (86B) engages distal notch (74) and will in unison drive needle (70) orbitally along an angular range of motion about 180 degrees back to its retracted position. Suture (73) (see FIG. 3A) will follow needle (70) and be threaded through the pierced tissue.

When first user input member (12) (see FIG. 1) is again released and the spring return opens the trigger, needle driver (86) again reciprocates through its return stroke where it orbits along an angular range of motion about 180 degrees clockwise back to its returned position as shown in FIG. 5A. During the return stroke, driver (86B) slides over needle (70). Thus, needle (70) is driven in a complete circular path spanning an angular range of 360° in response to first user input member (12) being actuated twice. The sequence may be repeated as needed by the surgeon to achieve the desired suturing task.

Further details, explanations, examples, and alternative embodiments of surgical suturing devices and subcomponents of the foregoing are disclosed in U.S. Pub. No. 2014/0171970, entitled "Circular Needle Applier with Articulating and Rotating Shaft," published Jun. 19, 2014, issued as U.S. Pat. No. 9,357,998 on Jun. 7, 2016, the disclosure of which is incorporated by reference herein; U.S. patent application Ser. No. 14/297,993, entitled "Jawed Cartridge Receiving Assembly for Needle Cartridge," filed Jun. 6, 2014, issued as U.S. Pat. No. 9,474,522 on Oct. 25, 2016, the disclosure of which is incorporated by reference herein; U.S. patent application Ser. No. 14/298,038, entitled "Circular Needle Applier with Cleats," filed Jan. 30, 2015, issued as U.S. Pat. No. 9,375,212 on Jun. 28, 2016, the disclosure of which is incorporated by reference herein; and U.S. patent application Ser. No. 14/740,724, entitled "Suturing Instrument with Motorized Needle Drive," filed Jun. 16, 2015, issued as U.S. Pat. No. 9,888,914 on Dec. 22, 2016, the disclosure of which is incorporated by reference herein. It should be understood that such details, explanations, examples, and alternative embodiments may be readily applied to the above-described instrument (10) and subcomponents thereof.

II. Exemplary Shaft Assembly Having a Jaw with an Integral Needle Cover

Simpler mechanical assemblies having a fewer number of components tend to be less complex, more efficient, and simpler to use than mechanical assemblies having a greater number of components. Particularly in a fast-paced, complex surgical procedure, simpler mechanical assemblies may reduce the cost of surgical instruments, reduce the likelihood of operator error, and generally improve patient outcomes. Thus, it may be desirable to consolidate one or more features between cartridge (30) and cartridge receiving assembly (50) and/or reduce the number of complex features therebetween in order to increase simplicity for the operator and reduce cost to the patient. For instance, rather than having needle cover (83), a cartridge (212) may have a disposable cover (214) that is configured to be removed and discarded prior to treatment. As such, cartridge receiving assembly (50) may be reconfigured for use during treatment in accordance with a cartridge receiving assembly (216) having an integral distal cover (216) that is configured to cover needle (70) of cartridge (212). Thus, disposable cover (214) captures needle (70) to a remainder of cartridge (212) prior to treatment, whereas cartridge receiving assembly (216) captures needle (70) to cartridge (212) during treatment.

Figure 7:
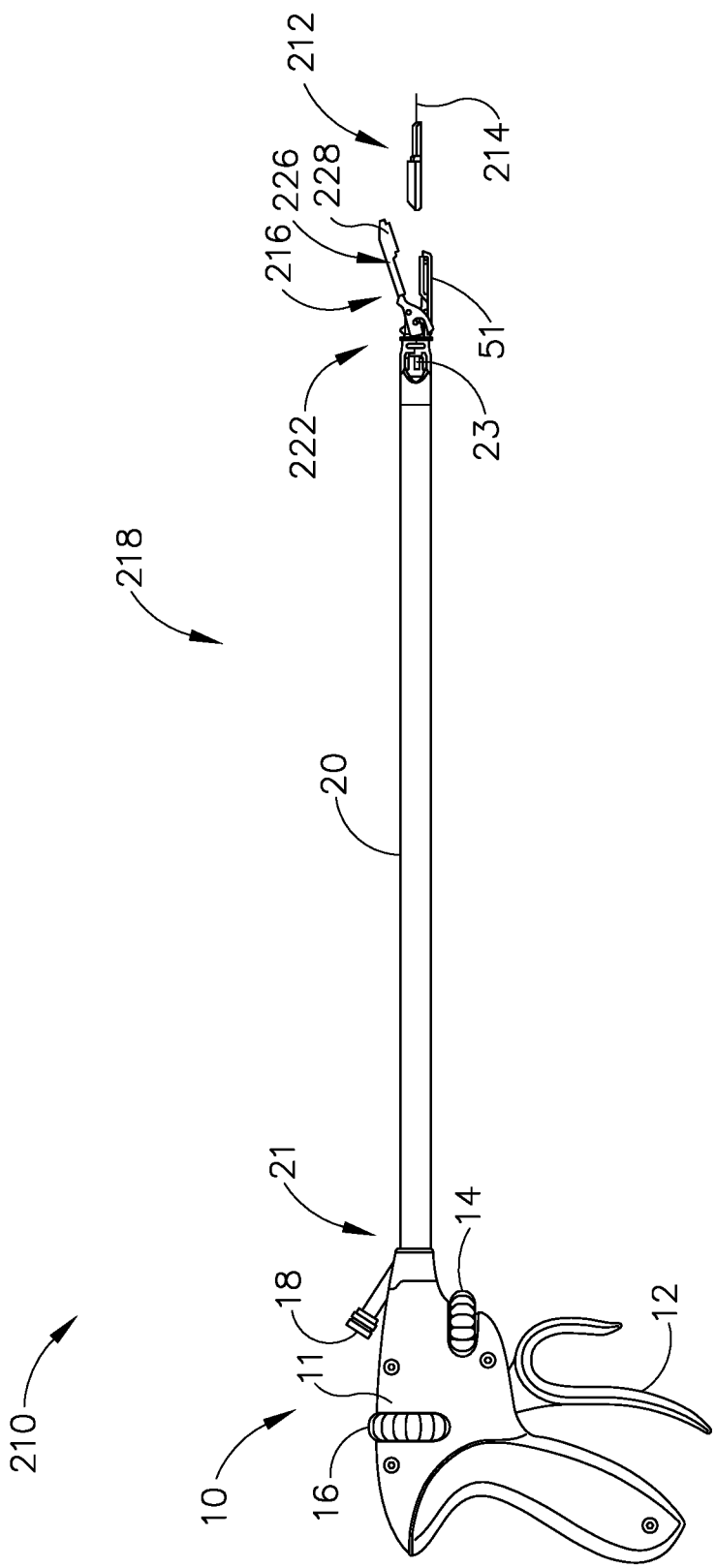
FIG. 7 depicts a side view of another exemplary surgical suturing instrument having another exemplary cartridge and another exemplary cartridge receiving assembly.

By way of example, a surgical suturing instrument (210) shown in FIG. 7 includes an example of cartridge (212) as well as an example of cartridge receiving assembly (216). Various examples of how instrument (2) (see FIG. 1) may be reconfigured to incorporate one or more features of cartridge (212) and cartridge receiving assembly (216) will be described in greater detail below; while other examples will be apparent to those of ordinary skill in the art according to the teachings herein. It should be understood that the examples described below may function substantially similar to instrument (2) described above. In particular, the surgical suturing instruments described below may be used to suture tissue. To this end, like numbers referenced below indicate like features discussed above in greater detail.

Figure 8:
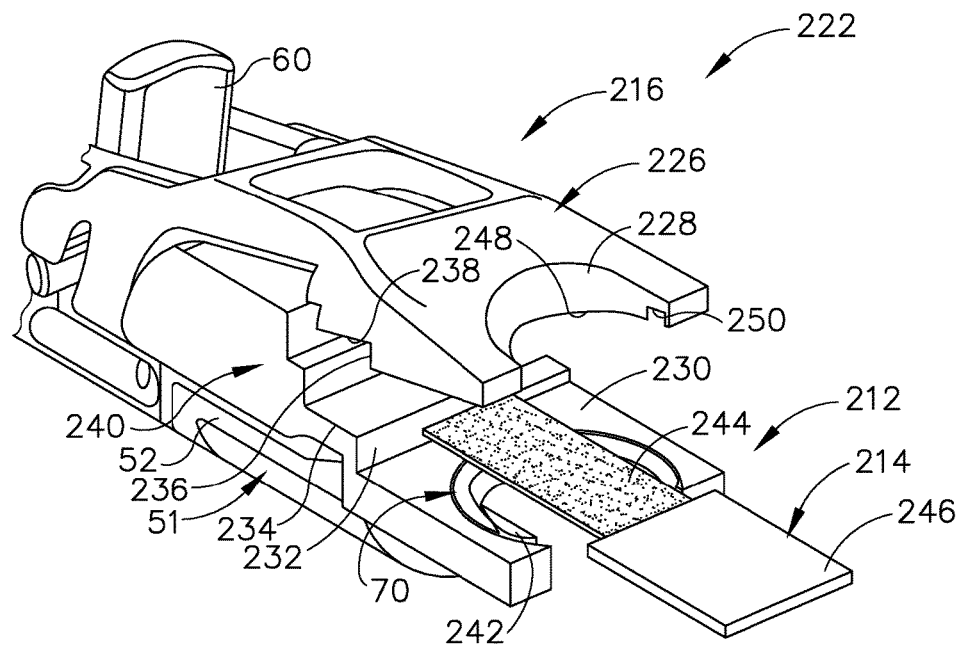
FIG. 8 depicts a front perspective view of the cartridge and the cartridge receiving assembly of FIG. 7, with the cartridge receiving assembly in an open position.

As shown in FIGS. 7-8, instrument (210) of the present example has a handle assembly (10) and a shaft assembly (218). Handle assembly (10) is connected to proximal end portion (21) of shaft assembly (218) as discussed above. In this example, distal end portion (222) of shaft (20) has cartridge receiving assembly (216) extending distally therefrom. Cartridge receiving assembly (216) includes lower jaw (51) and an upper jaw (226) pivotally connected to shaft (20) relative to lower jaw (51) for relative movement therebetween. In addition, button (60) of cartridge receiving assembly (216) is configured to selectively pivot upper jaw (226) relative to lower jaw (51) from an open position to a closed position and vice versa. Pivoting button (60) proximally will open jaws (51, 226), while pivoting button (60) distally will close jaws (51, 226).

FIG. 8 shows lower and upper jaws (51, 226) in the open position and cartridge (212) in greater detail. Lower jaw (51) includes longitudinal rails (52) that are configured to receive cartridge (212) and align cartridge (212) relative to lower and upper jaws (51, 226) for properly securing the cartridge (212) to cartridge receiving assembly (216). Upper jaw (226) has a distal extension (228) extending distally beyond lower jaw (226) and configured to engage a distal portion (230) of cartridge (212). To this end, distal portion (230) of cartridge (212) includes an alignment feature, such as guide edge (232) of guide tab (234), and distal extension (228) includes another alignment feature, such as guide edge (236) of guide slot (238). Guide tab (234) of cartridge (212) cooperates with guide slot (238) of distal extension (228) such that guide edge (236) of upper jaw (226) urges guide edge (232) of cartridge (212) into longitudinal alignment for closing jaws (51, 226), as shown in FIG. 9.

Figure 9:
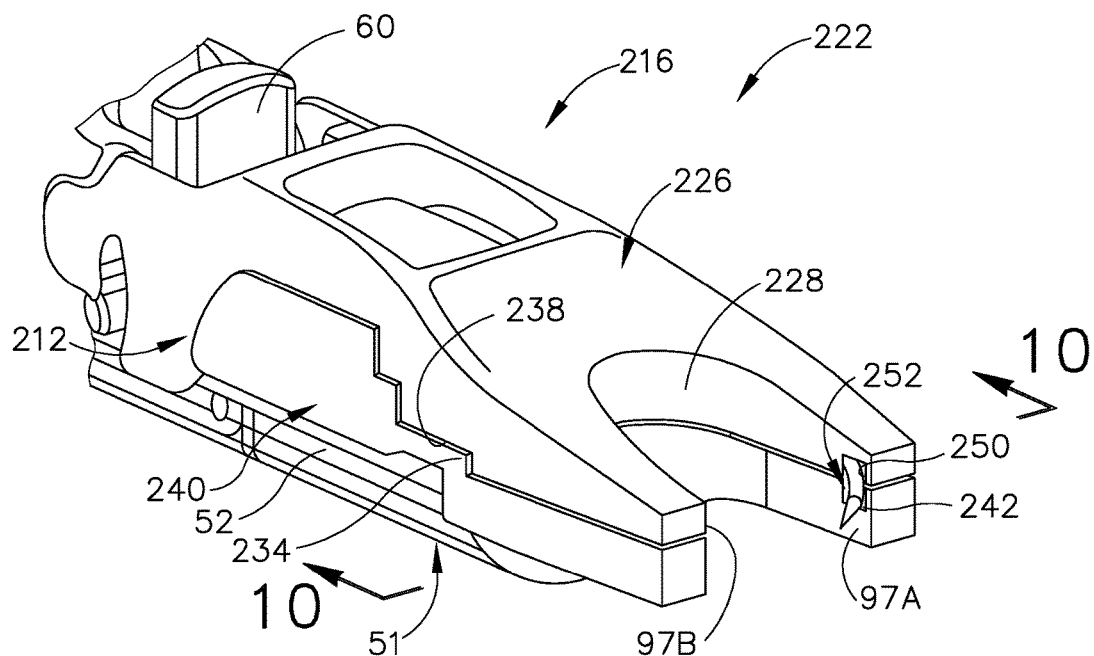
FIG. 9 depicts a front perspective view of the cartridge and the cartridge receiving assembly of FIG. 7, with the cartridge receiving assembly in a closed position.

With respect to FIGS. 8-9, cartridge (212) has a body (240), arcuate needle (70), and disposable cover (214). Distal portion (222) of body (240) has a cartridge groove (242) that is on an upper surface thereof and is configured to face upper jaw (226). Cartridge groove (240) has arcuate needle (70) resting therein for being actuated through carrier track (88) (see FIG. 5A) in use as described above in greater detail. Prior to installation, disposable cover (214) is releasably connected to cartridge (212) (e.g., via a pressure sensitive adhesive, etc.) with needle (70) secured to the body (240) therebetween. More particularly, disposable cover (214) has a film (244) and a grip tab (246) distally extending from film (244). Film (244) captures needle (70) within cartridge groove (242) between film (244) and body (240), whereas grip tab (246) is configured to be gripped and manipulated by the operator. Thereby, the grip tab is configured to be pulled by the operator to selectively remove the film (244) from the body (240) for installation of the cartridge within the cartridge receiving assembly (216) for use.

To this end, distal extension (228) of upper jaw (226) has a distal cover (248) that is configured to face cartridge (212) and capture needle (70) within cartridge groove (242) once disposable cover (248) has been removed from cartridge (212). Needle (70) is thus captured within cartridge groove (242) directly against upper jaw (226). More particularly, a jaw groove (250) extends through distal cover (248) and aligns with cartridge groove (242) in the closed position to similarly receive needle (70). Jaw and cartridge grooves (250, 242) collectively define a guide channel (252) that is configured generally surround the needle (70) and guide orbital movement of needle (70) during use. Guide channel (252) has exit and entrance ports (97A, 97B) from which needle actuates a forward direction for suturing tissue of the patient as discussed above in greater detail.

In some versions, film (244) has a thickness that is configured to effectively capture needle (70) prior to installation, but also allow for film (244) to be removed from between upper and lower jaws (226, 51). Film (244) and upper and lower jaws (226, 51) are thereby collectively configured to provide for removal of film (244) from upper and lower jaws (226, 51) in the closed position. For instance, upper jaw (226) may be configured to compress against lower jaw (51) with film (244) therebetween with a predetermined compression that allows for film (244) to slip along jaws (226, 51) for removal. Alternatively, closed jaws (226, 51) may define a predetermined gap such that film (244) is not compressed by closed jaws (226, 51) for removal of film (244).

FIGS. 10-12 show cartridge (212) further including a pair of blocker elements (254) that are configured to inhibit needle (70) from being actuated in a reverse direction. Needle (70) includes leading end portion (256) having an angled surface (257) and trailing end portion (258) having a transverse surface (259). Generally, user input member (12) (see FIG. 7) selectively actuates needle (70) in the forward direction such that trailing end portion (258) follows leading end portion (256) along the orbital path through guide channel (252). However, for various reasons, needle (70) may be inadvertently directed in the reverse direction. Blocker elements (254) are resiliently mounted adjacent to needle (70) and are configured to engage needle (70), thereby acting as one-way pawls to prevent needle (70) from traveling in the rearward direction.

Blocker elements (254) are resiliently mounted respectively within blind holes (260) that are respectively positioned proximate to exit and entrance ports (97A, 97B). In the present example, a biasing element (262), such as a coil spring, resiliently supports blocker element (254) in each blind hole (260) such that blocker elements (254) are configured to translate from an upward blocked position to a downward unblocked position. Each blocker element (254) is generally in the form of a cylindrical peg having an upper cam surface (264). In the forward direction, the angled surface of leading end portion (256) urges upper cam surface (264) downwardly from the blocked position to the unblocked position. The remainder of needle (70) may then continue to actuate in the forward direction with blocker element (254) biased against needle (70). As trailing end portion (258) slides over blocker element (254), needle (70) releases blocker element (254) to return to the blocked position.

In contrast, in the event that needle (70) actuates in the rearward direction, transverse surface (259) of trailing end portion (258) engages a sidewall (266) of blocker element (254) in the blocked position. As such, transverse surface (259) cannot urge blocker element (254) downwardly within the blind hole (260) and needle (70) is inhibited from actuating further in the rearward direction. It will be appreciated that at least some rearward direction of needle (70) may occur, but further rearward actuation will be halted depending on the position of blocker elements (254). It will be further appreciated that any number of blocker elements (254) may be used to reduce or increase potential rearward actuation of needle (70). As such, the invention is not intended to be limited to the specific blocker elements (254) described herein.

Figure 13A:
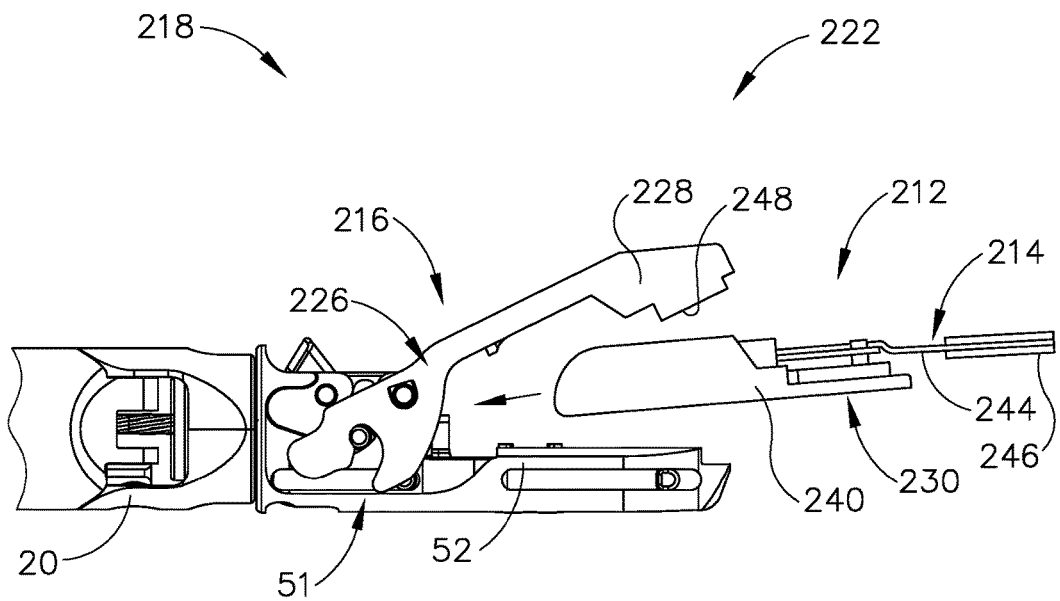
FIG. 13A depicts a side view of the cartridge receiving assembly of FIG. 7 in the open position receiving the cartridge of FIG. 7.
Figure 13B:
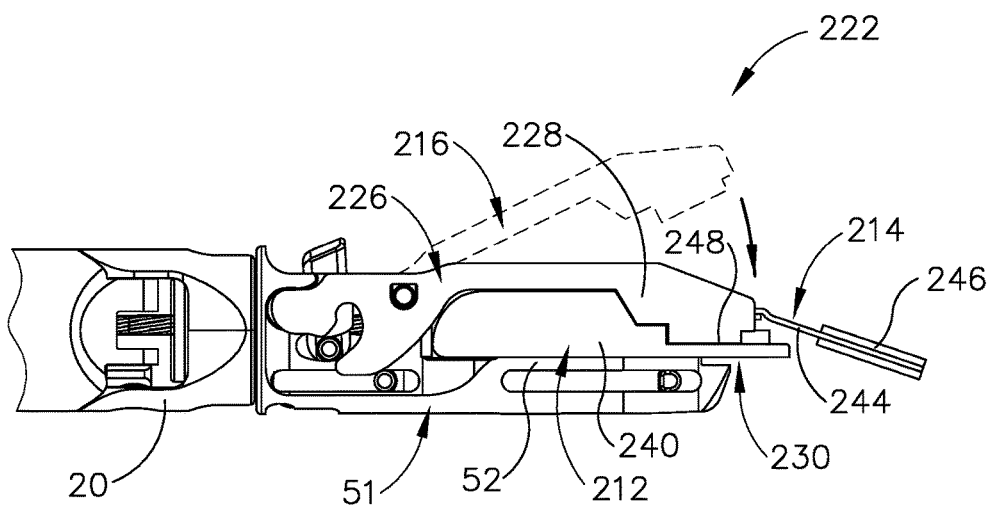
FIG. 13B depicts a side view of the cartridge receiving assembly of FIG. 7 in the closed position having received the cartridge of FIG. 7.
Figure 13C:
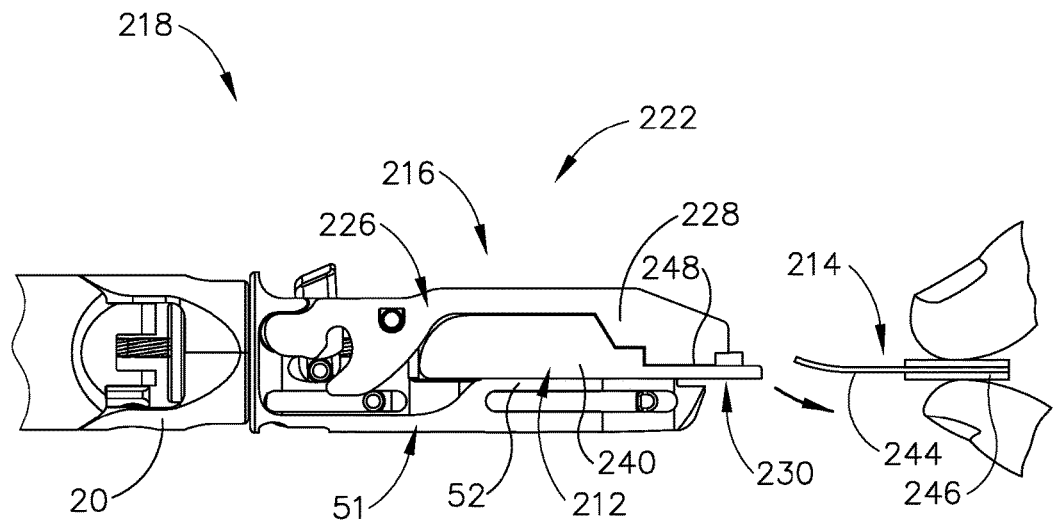
FIG. 13C depicts a side view of the cartridge receiving assembly of FIG. 7 in the closed position having received the cartridge of FIG. 7, with an operator removing a disposable needle cover from the cartridge.
Figure 13D:
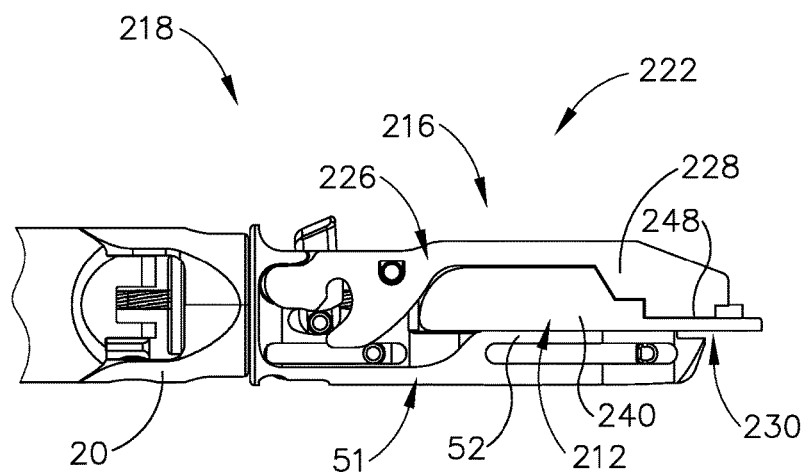
FIG. 13D depicts a side view of the cartridge receiving assembly of FIG. 7 in the closed position having received the cartridge of FIG. 7, with the disposable needle cover removed from the cartridge.
Figure 14:
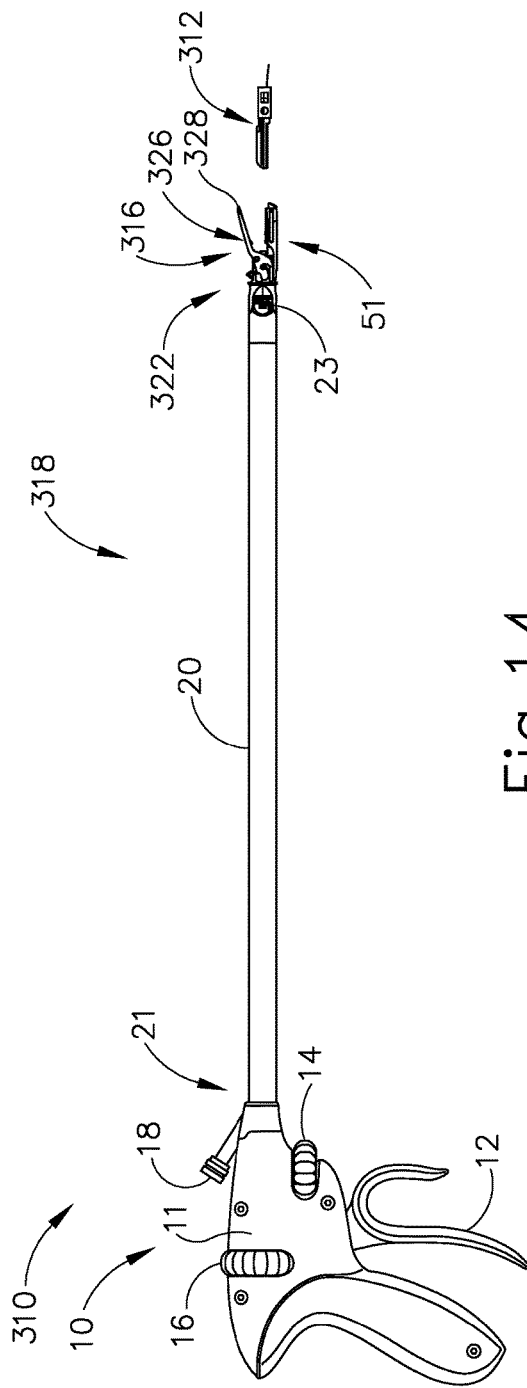
FIG. 14 depicts a side view of yet another exemplary surgical suturing instrument having yet another exemplary cartridge and yet another exemplary cartridge receiving assembly.

FIGS. 13A-13D illustrate installation of cartridge (212) with disposable cover (214) in cartridge receiving assembly (216). In use, upper jaw (226) is in the open position relative to lower jaw (51) as shown in FIG. 13A, and film (244) captures needle (70) to body (240) of cartridge (212). Jaws (226, 51) receive cartridge (212) therebetween and upper jaw (226) is selectively pivoted downwardly toward the closed position as shown in FIG. 13B. Alignment features, such as guide edges (232, 236) (see FIG. 8) cooperatively align cartridge (212) relative to jaws (226, 51) in the longitudinal direction such that cartridge groove (242) (see FIG. 8) aligns with jaw groove (250) (see FIG. 8)). As shown in FIG. 13C, the operator pulls on grip tab (246) thereby disconnecting film (244) from body (240) and releasing needle (70) (see FIG. 9) within guide channel (252) (see FIG. 8) collectively defined by cartridge and jaw grooves (242, 250). Distal cover (248) of upper jaw (226) captures needle (70) within guide channel (252) (see FIG. 8) as shown in FIG. 13D such that cartridge (212) is installed for suturing tissue in order to treat the patient as discussed above in greater detail.

In some versions of surgical suturing instrument (210), shaft assembly (218) and/or handle assembly (10) may be provided as being disposable or reusable. Versions with reusable components are intended to be cleaned, sterilized, and reused for multiple surgical procedures, and may include a flush port (not shown) to facilitate cleaning. In some such versions, the preferable life cycle of a reusable instrument may be at least 50 operations, more particularly at least 150 operations, or more particularly at least 200 operations. Reusable components may be built using materials that can withstand autoclave sterilization temperatures of at least 135 degrees Celsius, although low temperature materials can also be used with low temperature sterilization techniques known in the art.

III. Exemplary Shaft Assembly Having a Securement for Integral Release of Needle Cover In some instances, it may be desirable to release needle cover (83) from remainder of cartridge (30) for accessing needle (70) contained within cartridge (30) as shown in FIGS. 1-4. For example, the operator may desire to reset, repair, and/or replace needle (70) for improved treatment of the patient. Access to needle (70) requires release and complete removal of cage (87), which in some circumstances may be cumbersome and time consuming. In some instances, cartridge (30) may be provided with at least one of a securement and a distal extension, such as those discussed below, that hold needle cover (30) relative to remainder of cartridge (30) to provide for an integral release of needle cover (30) for accessing needle (70). It may be desirable to provide such a shaft assembly and cartridge so as to provide a disposable/reusable dichotomy. For instance, the replaceable cartridge may be provided as a disposable component while the handle assembly may be sterilized, reprocessed, reused, etc. Various examples of securements and distal extensions for integral release of various needle covers will be described in greater detail below; while other examples, such as those having various combinations of features described herein, will be apparent to those of ordinary skill in the art according to the teachings herein. It should be understood that the examples described below may function substantially similar to instruments (2, 210) described above. In particular, the surgical suturing instruments, cartridge receiving assemblies, and cartridges described below may be used to suture tissue. To this end, like numbers referenced below indicate like features discussed above in greater detail.

A. Exemplary Jaw with Distal Extension and Securement

FIGS. 14-18 illustrate a third exemplary surgical suturing instrument (310) with a third exemplary cartridge receiving assembly (316) and a third exemplary cartridge (312). As such, surgical instrument (310) includes handle assembly (10) and shaft assembly (318) with cartridge receiving assembly (316). Handle assembly (10) is connected to proximal end portion (21) of shaft assembly (318) as discussed above. In this example, distal end portion (322) of shaft (20) has cartridge receiving assembly (316) extending distally therefrom. Cartridge receiving assembly (316) includes lower jaw (51) and an upper jaw (326) pivotally connected to shaft (20) relative to lower jaw (51) for relative movement therebetween. In addition, button (60) of cartridge receiving assembly (316) is configured to selectively pivot upper jaw (326) relative to lower jaw (51) from an open position to a closed position and vice versa. Pivoting button (60) proximally will open jaws (51, 326), while pivoting button (60) distally will close jaws (51, 326).

Figure 15:
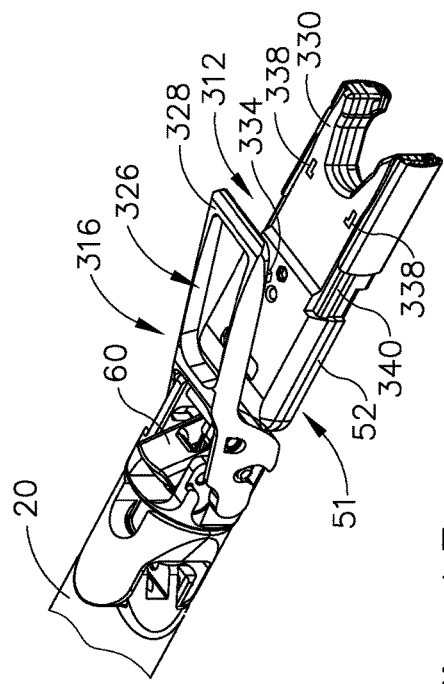
FIG. 15 depicts an enlarged upper perspective view of the cartridge and the cartridge receiving assembly of FIG. 14, with the cartridge receiving assembly in an open position.

FIGS. 15-17 show lower and upper jaws (51, 326) in the open position and cartridge (312) in greater detail. Lower jaw (51) includes longitudinal rails (52) that are configured to receive cartridge (312) and align cartridge (312) relative to lower and upper jaws (51, 326) for properly securing cartridge (312) to cartridge receiving assembly (316). Upper jaw (326) has a distal extension (328) extending distally beyond lower jaw (51) and configured to engage a needle cover (330) of cartridge (312). To this end, distal extension (328) includes a pair alignment features, such as guide surfaces (332) of guide tabs (334); and needle cover (330) includes another pair of alignment features, such as guide surfaces (336) of guide slots (338). Guide tabs (334) of upper jaw (326) cooperate respectively with guide slots (338) of needle cover (330) such that guide surfaces (336) of needle cover (330) urge guide surfaces (332) of upper jaw (326) into alignment for closing jaws (51, 326), as shown in FIG. 18.

A body (340) of cartridge (312) further includes a plurality of guide tabs (334) extending therefrom, and needle cover (330) has additional respective guide slots (238). Needle cover (330) is thus aligned with a predetermined alignment relative to upper jaw (326) and body (340). In the closed position of FIG. 18, guide tabs (334) releasably secure needle cover (330) relative to upper jaw (326) and body (340) in a horizontal plane, while distal extension (328) holds needle cover (330), such as by compression and/or fixed position, in a vertical plane. As such, alignment features (332, 334, 336, 338) form an integral guide securement releasably connecting needle cover (330) to body (340). In some versions, one or more guide tabs (334) are received within one or more respective guide slots (338) with a friction fit. In some other versions, one or more guide tabs (334) are received within one or more respective guide slots (338) with a slip fit. Of course, it will be appreciated that any combination of fits may be used in accordance with the invention described herein.

B. Exemplary Guide Securement and Removable Needle Cover

Figure 19:
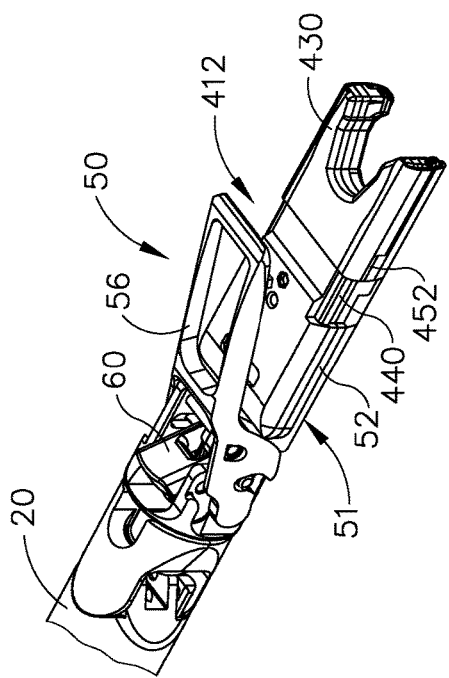
FIG. 19 depicts an enlarged perspective view of yet another exemplary cartridge and the cartridge receiving assembly of FIG. 1 in the open position.
Figure 20B:
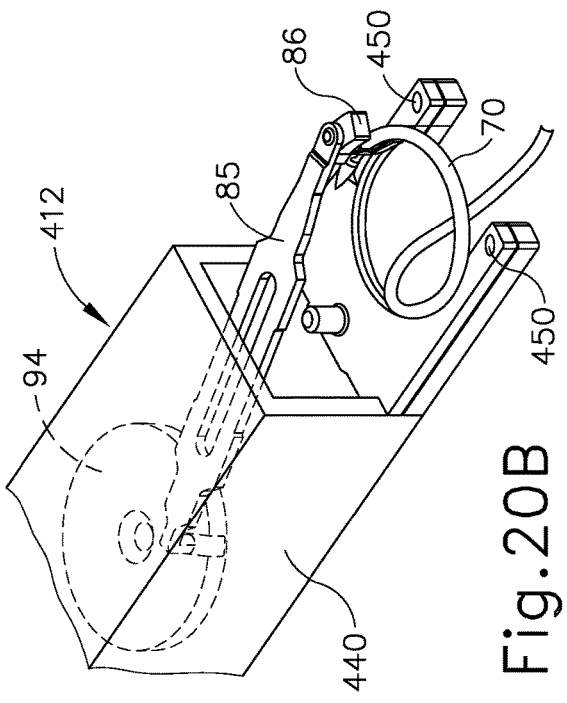
FIG. 20B depicts an enlarged perspective view of the cartridge of FIG. 19, with the needle cover removed from the cartridge.

FIGS. 19-20B illustrate cartridge receiving assembly (50) and a fourth exemplary cartridge (412). Cartridge receiving assembly (50) includes lower jaw (51) and upper jaw (56) pivotally connected to shaft (20) relative to lower jaw (51) for relative movement therebetween. In addition, button (60) of cartridge receiving assembly (50) is configured to selectively pivot upper jaw (56) relative to lower jaw (51) from an open position to a closed position and vice versa. Pivoting button (60) proximally will open jaws (51, 56), while pivoting button (60) distally will close jaws (51, 56).

Figure 20A:
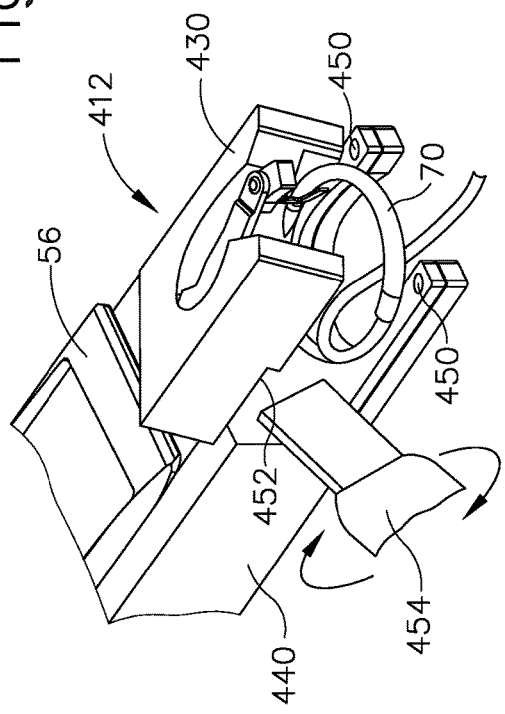
FIG. 20A depicts an enlarged perspective view of the cartridge and the cartridge receiving assembly of FIG. 19 in a closed position, with a needle cover being removed from the cartridge.

FIGS. 19-20A show lower and upper jaws (51, 56) in the open and closed positions, respectively, and cartridge (412) in greater detail. Lower jaw (51) includes longitudinal rails (52) that are configured to receive cartridge (412) and align cartridge (412) relative to lower and upper jaws (51, 326) for properly securing the cartridge (312) to cartridge receiving assembly (316).

Cartridge (412) includes a needle cover (430) frangibly connected to a body (440) by a frangible securement, such as one or more welds (450). As shown in FIG. 20A, needle cover (430) has a pry hole (440) that is configured to receive a pry tool (454), such as a flathead screwdriver, such that pry tool (454) may be operated by the operator to direct needle cover (430) away from body (440). Upon application of a sufficient force between needle cover (430) and body (440), welds (450) will break in tension and needle cover (430) will release from body (440) as shown in FIG. 20B. More particularly, in the present example, needle cover (430) may be completely removed from body (440). As such, welds (450) form an integral frangible securement releasably connecting needle cover (430) to body (440).

C. Exemplary Frangible Securement and Releasable Needle Cover with Integral Living Hinge FIG. 21 illustrates a fifth exemplary cartridge (512). Cartridge (512) includes a needle cover (530) that is frangibly and hingedly connected to a body (540) by a frangible securement, such as one or more welds (450), and a hinge (548), respectively. As shown in FIG. 21, needle cover (530) has pry hole (440) that is configured to receive pry tool (454) (see FIG. 20A), such as a flathead screwdriver, such that pry tool (454) (see FIG. 20A) may be operated by the operator to direct needle cover (530) away from body (540). Upon application of a sufficient force between needle cover (530) and body (540), welds (450) will break in tension and needle cover (530) will release from body (540) as shown in FIG. 21. In one example, hinge (548) is in the form of a living hinge (548) extending between upper surfaces of body (540) and needle cover (530). Released needle cover (530) thereby pivots upwardly about living hinge (548) for accessing needle (70).

D. Exemplary Frangible Securement and Releasable Needle Cover with Integral Strap Hinge FIGS. 22A-22B illustrate cartridge receiving assembly (50) and a sixth exemplary cartridge (612). Cartridge (612) includes a needle cover (630) that is frangibly and hingedly connected to a body (640) by a frangible securement, such as one or more welds (450), and a hinge (648), respectively. As shown in FIG. 22A, needle cover (630) has pry hole (440) that is configured to receive pry tool (454) (see FIG. 20A), such as a flathead screwdriver, such that pry tool (454) (see FIG. 20A) may be operated by the operator to direct needle cover (630) away from body (640). Upon application of a sufficient force between needle cover (630) and body (640), welds (450) will break in tension and needle cover (630) will release from body 6540) as shown in FIG. 22B. In the present example, hinge (648) is in the form of an integral strap hinge (648) extending between lower side surfaces of body (640) and needle cover (630). Released needle cover (630) thereby pivots sidewardly about integral strap hinge (648) for accessing needle (70).

E. Exemplary Jaw with Distal Extension, Frangible Securement, and Releasable Needle Cover with Integral Strap Hinge FIGS. 23-24B illustrate a fourth exemplary cartridge receiving assembly (716) and a seventh exemplary cartridge (712). Cartridge receiving assembly (716) includes lower jaw (51) and an upper jaw (726) pivotally connected to shaft (20) relative to lower jaw (51) for relative movement therebetween. In addition, button (60) of cartridge receiving assembly (716) is configured to selectively pivot upper jaw (726) relative to lower jaw (51) from an open position to a closed position and vice versa. Pivoting button (60) proximally will open jaws (51, 726), while pivoting button (60) distally will close jaws (51, 726).

FIG. 23 shows lower and upper jaws (51, 726) in the open position and cartridge (712). Lower jaw (51) includes longitudinal rails (52) that are configured to receive cartridge (712) and align cartridge (712) relative to lower and upper jaws (51, 726) for properly securing cartridge (712) to cartridge receiving assembly (716). Upper jaw (726) has a distal extension (728) extending distally beyond lower jaw (51) and configured to engage a needle cover (630) of cartridge (712).

Cartridge (712) includes needle cover (630) hingedly connected to body (640) by hinge (648). Notably, cartridge (712) does not include a frangible securement holding needle cover (630) to body (640) in this particular example. Rather, distal extension (728) of upper jaw (726) holds needle cover (630) to body (640) in the closed position shown in FIG. 24A. As shown in FIG. 24B, needle cover (630) has pry hole (440) that is configured to receive pry tool (454), such as a flathead screwdriver, such that pry tool (454) may be operated by the operator to direct needle cover (630) away from body (640) with jaws (51, 726) in the open position. In other words, hinge (648) secures needle cover (630) relative to body (640) in the horizontal plane, while upper jaw (726) holds needle cover (630), such as by compression and/or fixed position, in the vertical plane. Hinge (648) thus is a securement in combination with upper jaw (726) to releasably connect needle cover (630) to body (640).

F. Exemplary Jaw with Distal Extension, Securement, and Releasable Needle Cover with Integral Strap Hinge FIGS. 25-26B illustrate a fifth exemplary cartridge receiving assembly (816) and an eighth exemplary cartridge (812). Cartridge receiving assembly (816) includes a lower jaw (824) and an upper jaw (826), each of which extends distally to engage the entire top and bottom surfaces of cartridge (812). FIG. 25 shows lower and upper jaws (824, 826) in the open position and cartridge (812). Lower jaw (824) includes longitudinal rails (856) that are configured to receive cartridge (812) and align cartridge (812) relative to lower and upper jaws (824, 826) for properly securing cartridge (812) to cartridge receiving assembly (816). Upper jaw (826) has a distal extension (828) that is configured to engage a needle cover (830) of cartridge (812). To this end, needle cover (830) includes a pair of alignment features, such as guide edges (832) of guide tabs (834); and distal extension (828) includes another pair of alignment features, such as guide edges (836) of guide slots (838). Guide tabs (834) of needle cover (830) cooperate respectively with guide slots (838) of upper jaw (826) such that guide edges (836) of upper jaw (826) urge guide edges (832) of needle cover (830) into alignment for closing jaws (824, 826), as shown in FIG. 26A.

In the closed position of FIG. 26A, guide tabs (834) releasably secure needle cover (830) relative to upper jaw (826) and body (840) in a horizontal plane, while distal extension (828) holds needle cover (330), such as by compression and/or fixed position, in a vertical plane. As such, alignment features (832, 834, 836, 838) form an integral guide securement releasably connecting needle cover (830) to body (840) while jaws (824, 826) are in the closed position.

G. Exemplary Jaw and Clamp Securement

FIGS. 27-31 illustrate a fourth exemplary surgical suturing instrument (1010) with a sixth exemplary cartridge receiving assembly (1016) and a ninth exemplary cartridge (1012). Surgical suturing instrument (1010) further includes a suture dispenser packaging (900) to releasably contain cartridge (1012) with a length of suture (973). Cartridge (1012) is configured and operable substantially similar to cartridge (30), and contains needle (70) (see FIG. 30), a length of suture (973) connected to needle (70) (see FIG. 30), a needle driver (e.g., needle driver (86) (see FIGS. 5A-5C)) that is operative to engage and move the needle (70) (see FIG. 30) relative the cartridge (1012), and a drive assembly that is operatively connected to the needle driver. Cartridge (1012) may thus be readily received in cartridge receiving assembly (1016) and may thereby be actuated by instrument (1010). Needle (70) (see FIG. 30) is initially provided in cartridge (1012) in a retracted position (e.g., the position shown in FIG. 5A).

In the example shown, the length of suture (973) comprises barbed suture, with a plurality of barbs (975). Suture (973) is contained on a spool (908), as discussed in further detail below. By way of example only, suture (973), spool (908), and/or other features of packaging (900) may be constructed in accordance with at least some of the teachings of U.S. patent application Ser. No. 14/741,635, entitled "Barbed Suture Dispenser," filed Jun. 17, 2015, issued as U.S. Pat. No. 10,070,858 on Sep. 11, 2018, the disclosure of which is incorporated by reference herein. However, it will be understood that packaging (900) is configured for use with all types of sutures, including barbed and non-barbed sutures; and that the components of packaging (900) may be configured and arranged in numerous other ways.

Packaging (900) of the present example includes a housing (903) comprising a top sheet or lid (901) and a shell (902). Housing (903) has a proximal end (904) and a distal end (906). In the present example, shell (903) includes a greater depth at distal end (906) to accommodate spool (908). Housing (903) further includes a first side (910) and a second side (912). Proximal end (904) includes a pair of opposing arms (914) defining a gap or recess (916) therebetween. As shown in the present example, cartridge (1012) is received in gap (916) such that cartridge (1012) is frictionally held by arms (914). In addition or in the alternative, packaging (900) may include one or more latches, clips, clamping features, and/or any other suitable kinds of features that may releasably retain cartridge (1012) relative to housing (903). Packaging (900) further includes a flange (918) extending at an oblique angle relative to a central longitudinal axis of shell (902). Flange (918) includes a hook-shaped portion (920) positioned in shell (902). Hook-shaped portion (920) is sized and configured to be at least partially received between arms (see FIG. 4) of cartridge (1012) such that the frictional engagement between arms (see FIG. 4) and hook-shaped portion (920) also maintains cartridge (1012) relative to packaging (900).

Referring to FIGS. 28-29, spool (908) includes a first flange (922), a second flange (924), and a generally cylindraceous body (926) therebetween. As shown, spool (908) includes a central channel (930) that receives a rod (not shown) extending from shell (902) that is fixed to shell (902). Spool (908) extends along an axis (not shown). In the example shown, spool (908) is configured to rotate about the rod and axis (913) to release suture (972) as cartridge (1012) is pulled away from packaging (900). However, in some examples, spool (908) may be fixedly connected to a rod or other structure that is configured to rotate relative to housing (903). In the present example, a leading end of suture (973) is connected to needle (70) (see FIG. 30) and trailing end of suture (973) is disposed on spool (908).

Once cartridge (1012) is secured in cartridge receiving assembly (1016) of instrument (1010) in the manner described above, withdrawing shaft (20) will pull cartridge (1012) from packaging (900), and suture (973) will reel out from spool (908). Particularly, the frictional engagement between suture (973) and a helical channel (928) will cause a rotation of spool (908) upon the sufficient pulling force of suture (973). In the present example, trailing end of suture (973) is removably coupled to spool (908) in a manner that allows suture (973) to remain coupled to spool (908) absent a sufficient pulling force from the operator. However, upon the application of a sufficient force, trailing end of suture (973) may be removed from spool (908) after the remainder of suture (973) has reeled off of spool (908), and thus suture (973) will be ready for use in a suturing operation. Suturing instrument (1010) with cartridge (1012) loaded in cartridge receiving assembly (1016) will operate in the same manner as suturing instrument (2) with cartridge (30) loaded in cartridge receiving assembly (50) as described above. In any case, further details, explanations, examples, and alternative embodiments of surgical suturing devices and subcomponents of the foregoing are disclosed in U.S. application Ser. No. 14/741,635, issued as U.S. Pat. No. 10,070,858 on Sep. 11, 2018, entitled "Barbed Suture Dispenser," filed Jun. 17, 2015, the disclosure of which is incorporated by reference herein.

With respect to FIG. 30, shell (902) operatively connects to cartridge receiving assembly (1016) via securements, such as clamps (1058), that are releasably secured to cartridge (1012). In the present example, each clamp (1058) includes a pair of clips (1060) extending inwardly from an inward facing sidewall (1062) of shell (902). Shell (902) more specifically includes offset clips (1060) extending inwardly from sidewall (1062) of first side (910); as well as offset clips (1060) extending inwardly from sidewall (1062) of second side (912). In other words, sidewalls (1062) and clips (1060) define two inwardly opening clamps (1058). Cartridge (1012) includes a needle cover (1030) and a body (1040). Needle cover (1030) and body (1040) are configured to be received within clamps (1058) such that clips (1060) effectively compress needle cover (1030) against body (1040) in order to releasably secure needle cover (1030) to body (1040). As such, in the present example, in the event that clamps (1058) are removed from cartridge (1012), needle cover (1030) would simply be resting on body (1040), and the operator may remove needle cover (1030) from body (1040) regardless of the position of jaws (1024, 1026).

Shell (902) operatively aligns with cartridge receiving assembly (1016) via the interface between cartridge (1012) and cartridge receiving assembly (1016) as shown in FIG. 31. Lower jaw (1024) includes longitudinal rails (1056) that are configured to receive cartridge (1012) and align cartridge (1012) relative to lower and upper jaws (1024, 1026) for properly securing cartridge (1012) to cartridge receiving assembly (1016). Upper jaw (1026) and upper portion of body (1040) include various alignment features for further alignment. To this end, upper portion of body (1040) includes guide edges (1032) of guide tabs (1034), and upper jaw (1028) includes guide edges (1036) of guide slots (1038). Guide tabs (1034) of upper portion of body (1040) cooperate respectively with guide slots (1038) of upper jaw (1026) such that guide edges (1036) of upper jaw (1026) urge guide edges (1032) of upper portion of body (1040) into alignment for closing jaws (1024, 1026), as shown in FIG. 31.

In some versions of surgical suturing instruments (310, 1010), cartridges (312, 412, 512, 612, 712, 812, 1012) and/or cartridge receiving assemblies (316, 716, 816, 1016) may be provided as being disposable or reusable. Versions with reusable components are intended to be cleaned, sterilized, and reused for multiple surgical procedures, and may include a flush port (not shown) to facilitate cleaning. In some such versions, the preferable life cycle of a reusable instrument may be at least 50 operations, more particularly at least 150 operations, or more particularly at least 200 operations. Reusable components may be built using materials that can withstand autoclave sterilization temperatures of at least 135 degrees Celsius, although low temperature materials can also be used with low temperature sterilization techniques known in the art.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A surgical instrument, comprising: (a) a body having an actuator; (b) a shaft extending distally from the body; and (c) a cartridge receiving assembly projecting from a distal end portion of the shaft, wherein the cartridge receiving assembly comprises: (i) a first jaw, and (ii) a second jaw, wherein the first jaw is movable relative to the second jaw between an open position and a closed position, wherein the first and second jaws are configured to receive a suture cartridge therebetween when the first jaw is in the open position, wherein the first and second jaws are configured to secure a suture cartridge therebetween and thereby operatively couple the actuator with the suture cartridge when the first jaw is in the closed position, wherein the first jaw is further configured to receive a needle of the suture cartridge directly thereagainst when the first jaw is in the closed position such that the first jaw is configured to capture the needle within the suture cartridge.

EXAMPLE 2

The surgical instrument of Example 1, wherein the first jaw has a distal cover that is configured to receive the needle directly thereagainst, wherein the distal cover extends distally beyond a distal end of the second jaw.

EXAMPLE 3

The surgical instrument of any one or more of Examples 1 through 2, wherein the first jaw has a jaw groove configured to receive the needle in the closed position for capturing the needle and guiding actuation therein.

EXAMPLE 4

The surgical instrument of any one or more of Examples 1 through 3, wherein the second jaw is pivotally fixed relative to the distal end portion of the shaft.

EXAMPLE 5

The surgical instrument of any one or more of Examples 1 through 4, wherein the cartridge receiving assembly further comprises a rotary drive output configured to mate with a rotary drive input of a suture cartridge captured between the first and second jaws.

EXAMPLE 6

The surgical instrument of Example 5, wherein the cartridge receiving assembly is configured to convert motion of the actuator into rotation of the rotary drive output.

EXAMPLE 7

The surgical instrument of any one or more of Examples 1 through 6, further comprising a suture cartridge, wherein the suture cartridge comprises: (i) a cartridge body, (ii) a disposable cover removably connect to the cartridge body, and (iii) a needle positioned between the disposable cover and the cartridge body and contained in the cartridge body by the disposable cover, wherein the disposable cover is removable from the cartridge body to release the needle relative to the cartridge body for being operatively actuated via the actuator.

EXAMPLE 8

The surgical instrument of Example 7, wherein the disposable cover comprises a film, wherein the needle is positioned between the film and the cartridge body, wherein the film is removably connected to the cartridge body for securing the needle to the cartridge body.

EXAMPLE 9

The surgical instrument of Example 8, wherein the disposable cover includes a grip tab extending from the film, wherein the grip tab is configured to be grasped by an operator to remove the film from the cartridge body.

EXAMPLE 10

The surgical instrument of any one or more of Examples 8 through 9, wherein the film is removably connected to the cartridge body via an adhesive.

EXAMPLE 11

The surgical instrument of any one or more of Examples 7 through 10, wherein the first jaw and the cartridge body are configured to together define a gap sized to accommodate the disposable cover without compressing the disposable cover between the first jaw and the cartridge body when the first jaw is in the closed position.

EXAMPLE 12

The surgical instrument of any one or more of Examples 7 through 11, wherein the suture cartridge further comprises a blocker element positioned adjacent to the needle, wherein blocker element is configured to engage the needle to prevent the needle from traveling in a first orbital direction while permitting the needle to travel in a second orbital direction.

EXAMPLE 13

The surgical instrument of Example 12, wherein the blocker element is resiliently mounted to the body and is configured to move between a blocked position and an unblocked position, wherein in the blocked position the blocker element is configured to engage the needle to inhibit the needle from traveling in the first orbital direction, and wherein in the unblocked position the blocker element is configured to permit the needle to travel in the second orbital direction.

EXAMPLE 14

The surgical instrument of Example 13, wherein the needle has a leading end portion and a trailing end portion, wherein the leading end portion is configured to urge the blocker element from the blocked position to the unblocked position while actuating in the second orbital direction, wherein the trailing end portion is configured to engage the blocker element and inhibit the needle from actuating in the first orbital direction.

EXAMPLE 15

The surgical instrument of any one or more of Examples 7 through 14, wherein the cartridge body defines a groove, wherein the needle is positioned in the groove of the cartridge body, wherein the first jaw has a jaw groove complementing the groove of the cartridge body, wherein the needle is operable to orbit along the jaw groove and the groove of the cartridge body when the first jaw is in the closed position.

EXAMPLE 16

A surgical instrument, comprising: (a) a shaft having a proximal end portion and a distal end portion; (b) a cartridge having a suturing needle; and (c) a cartridge receiving assembly projecting distally from the distal end portion of the shaft, the cartridge receiving assembly comprising: (i) a lower jaw, and (ii) an upper jaw, wherein the lower and upper jaws are configured to transition between an open configuration and a closed configuration, wherein the lower and upper jaws are configured to receive the cartridge therebetween when the lower and upper jaws are in the open configuration, wherein the lower and upper jaws are configured to secure the cartridge therebetween when the lower and upper jaws are in the closed configuration, wherein at least one of the lower jaw or the upper jaw is configured to receive the needle directly thereagainst when the lower and upper jaws are in the closed configuration such that the at least one of the lower jaw or the upper jaw is configured to capture the needle within the cartridge.

EXAMPLE 17

A cartridge for a surgical suturing instrument having a user input member, the cartridge comprising: (a) a cartridge body; (b) a disposable cover removably connect to the cartridge body; and (c) a needle positioned between the disposable cover and the cartridge body and contained in the body by the disposable cover, the disposable cover is removable from the body to release the needle relative to the body for being operatively actuated via the user input member to suture a tissue of a patient.

EXAMPLE 18

The cartridge of Example 17, wherein the disposable cover comprises a film, wherein the needle is positioned between the film and the body, wherein the film is removably adhered to the cartridge body for containing the needle in the cartridge body.

EXAMPLE 19

The cartridge of Example 18, wherein the disposable cover includes a grip tab extending from the film, wherein the grip tab is configured to be grasped by an operator for removing the film from the cartridge body.

EXAMPLE 20

The cartridge of any one or more of Examples 17 through 19, further comprising a blocker element positioned adjacent to the needle, and blocker element is configured to engage the needle to inhibit the needle from actuating in a reverse direction.

EXAMPLE 21

A surgical instrument, comprising: (a) a body having an actuator; (b) a shaft extending distally from the body; (c) a cartridge receiving assembly at a distal portion of the shaft, wherein the cartridge receiving assembly comprises: (i) a first jaw, and (ii) a second jaw, wherein the first and second jaws are configured to transition between an open configuration and a closed configuration; and (d) a suture cartridge, wherein the suture cartridge comprises: (i) a cartridge body, (ii) a needle supported by the cartridge body, and (iii) a needle cover, wherein the needle cover is releasably connected to the cartridge body such that the needle cover surrounds at least a portion of the needle, wherein the needle cover is releasably connected to the body by at least one of: (A) a securement, wherein the securement is located between the needle cover and the cartridge body to releasably connect the needle cover to the cartridge body, or (B) a distal extension, wherein the distal extension projects from at least one of the first jaw or the second jaw and is configured to engage the needle cover thereby holding the needle cover to the cartridge body in the closed position; wherein the first and second jaws are configured to receive the suture cartridge when the first and second jaws are in the open configuration; wherein the first and second jaws are configured to capture the suture cartridge and operable couple the suture cartridge with the actuator when the first and second jaws are in the closed configuration.

EXAMPLE 22

The surgical instrument of Example 21, wherein the needle cover is releasably connected to the cartridge body by the securement.

EXAMPLE 23

The surgical instrument of Example 22, wherein the securement comprises a guide securement including a first guide member and a second guide member, the first guide member defined by the body, wherein the second guide member is defined by the needle cover, wherein one of the first guide member or the second guide member is configured to releasably receive the other of the first guide member or the second guide member.

EXAMPLE 24

The surgical instrument of Example 23, wherein the first guide member is in the form of a peg, wherein the second guide member defines a hole configured to receive the peg.

EXAMPLE 25

The surgical instrument of Example 24, wherein the peg is configured to be received within the hole of the second guide member with a friction fit.

EXAMPLE 26

The surgical instrument of any one or more of Examples 22 through 25, wherein the securement comprises a frangible securement.

EXAMPLE 27

The surgical instrument of Example 26, wherein the frangible securement is in the form of a weld.

EXAMPLE 28

The surgical instrument of any one or more of Examples 22 through 27, wherein the securement comprises a clamp engaged with the needle cover and the cartridge body, wherein the clamp is configured to compress the needle cover against the cartridge body.

EXAMPLE 29

The surgical instrument of any one or more of Examples 21 through 28, wherein the needle cover is releasably connected to the cartridge body by the distal extension.

EXAMPLE 30

The surgical instrument of Example 29, wherein the distal extension projects from the first jaw.

EXAMPLE 31

The surgical instrument of Example 30, wherein the distal extension is configured to compress the needle cover against the cartridge body.

EXAMPLE 32

The surgical instrument of any one or more of Examples 21 through 31, wherein the needle cover includes a first alignment feature and the cartridge body includes a second alignment feature, wherein the first and second alignment features are configured to cooperate such that the needle cover is positioned relative to the cartridge body with a predetermined alignment.

EXAMPLE 33

The surgical instrument of Example 32, wherein first alignment feature comprises a slot defined by the needle cover, wherein second alignment feature comprises a tab defined by the cartridge body, wherein the slot is configured to receive the tab for aligning the needle cover relative to the cartridge body.

EXAMPLE 34

The surgical instrument of any one or more of Examples 21 through 33, wherein the needle cover includes a first alignment feature and at least one of the first jaw or the second jaw includes a second alignment feature, wherein the first and second alignment features are configured to cooperate such that the needle cover is positioned relative to the at least one of the first jaw or the second jaw with a predetermined alignment for holding the needle cover to the cartridge body in the closed position.

EXAMPLE 35

The surgical instrument of Example 34, wherein the first alignment feature comprises a slot defined by the needle cover, wherein the second alignment feature comprises a tab defined by the at least one of the first jaw or the second jaw, wherein the slot is configured to receive the tab for aligning the needle cover relative to the at least one of the first jaw or the second jaw.

EXAMPLE 36

A surgical instrument, comprising: (a) a shaft having a proximal end portion and a distal end portion; (b) a cartridge receiving assembly projecting distally from the distal end portion of the shaft, the cartridge receiving assembly comprising: (i) a first jaw, and (ii) a second jaw, wherein the second jaw has a distal extension; and (c) a suture cartridge configured to be received and captured between the first jaw and the second jaw, the suture cartridge comprising: (i) a cartridge body, (ii) a needle supported by the cartridge body, (iii) a needle cover, wherein the needle cover is movably connected to the cartridge body such that the needle cover surrounds at least a portion of the needle, and (iv) a securement, wherein the securement is integral with one or both of the cartridge body or the needle cover, wherein the needle cover is connected to the cartridge body by at least one of the securement or the distal extension.

EXAMPLE 37

The surgical instrument of Example 36, wherein the needle cover is releasably connected to the cartridge body by the securement, wherein the securement is positioned between the needle cover and the cartridge body to releasably connect the needle cover to the cartridge body.

EXAMPLE 38

The surgical instrument of any one or more of Examples 36 through 37, wherein the needle cover is releasably connected to the body by the distal extension, wherein the distal extension is configured to engage the needle cover thereby holding the needle cover to the body.

EXAMPLE 39

The surgical instrument of any one or more of Examples 36 through 38, wherein the needle cover is releasably connected to the cartridge body by the securement, wherein the upper jaw terminates at a distal end, wherein the distal end of the upper jaw is located proximal to the securement when the cartridge is captured between the lower and upper jaws.

EXAMPLE 40

A cartridge for a surgical suturing instrument having an upper jaw and a lower jaw for receiving the cartridge, comprising: (a) a needle; (b) a body supporting the needle thereon; (c) a needle cover releasably connected to the body such that the needle cover surrounds at least a portion of the needle; and (d) a securement coupling the needle cover with the body, wherein the body defines a slot configured to receive a cover removing tool, wherein a cover removing tool inserted in the slot is operable to at least partially decouple the needle cover from the body.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein, is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
   (a) a body having an actuator;
   (b) a shaft extending distally from the body; and
   (c) a cartridge receiving assembly projecting from a distal end portion of the shaft, wherein the cartridge receiving assembly comprises:
   a first jaw, and
   (ii) a second jaw,
   wherein the first jaw is movable relative to the second jaw between an open position and a closed position,
   wherein the first and second jaws are configured to receive a suture cartridge therebetween when the first jaw is in the open position,
   wherein the first and second jaws are configured to secure a suture cartridge therebetween and thereby operatively couple the actuator with the suture cartridge when the first jaw is in the closed position,
   wherein the first jaw is further configured to receive a needle of the suture cartridge directly thereagainst and capture the needle between the first and second jaws along a circular path when the first jaw is in the closed position such that the first jaw is configured to capture the needle within the suture cartridge while the needle orbits along the circular path between the first and second jaws.

2. The surgical instrument of claim 1, wherein the first jaw has a distal cover that is configured to receive the needle directly thereagainst, wherein the distal cover extends distally beyond a distal end of the second jaw.

3. The surgical instrument of claim 1, wherein the first jaw has a jaw groove configured to receive the needle in the closed position for capturing the needle and guiding actuation therein.

4. The surgical instrument of claim 1, wherein the second jaw is pivotally fixed relative to the distal end portion of the shaft.

5. The surgical instrument of claim 1, wherein the cartridge receiving assembly further comprises a rotary drive output configured to mate with a rotary drive input of a suture cartridge captured between the first and second jaws.

6. The surgical instrument of claim 5, wherein the cartridge receiving assembly is configured to convert motion of the actuator into rotation of the rotary drive output.

7. The surgical instrument of claim 1, further comprising a suture cartridge, wherein the suture cartridge comprises:
   (i) a cartridge body,
   (ii) a disposable cover removably connect to the cartridge body, and
   (iii) a needle positioned between the disposable cover and the cartridge body and contained in the cartridge body by the disposable cover, wherein the disposable cover is removable from the cartridge body to release the needle relative to the cartridge body for being operatively actuated via the actuator.

8. The surgical instrument of claim 7, wherein the disposable cover comprises a film, wherein the needle is positioned between the film and the cartridge body, wherein the film is removably connected to the cartridge body for securing the needle to the cartridge body.

9. The surgical instrument of claim 8, wherein the disposable cover includes a grip tab extending from the film, wherein the grip tab is configured to be grasped by an operator to remove the film from the cartridge body.

10. The surgical instrument of claim 8, wherein the film is removably connected to the cartridge body via an adhesive.

11. The surgical instrument of claim 7, wherein the first jaw and the cartridge body are configured to together define a gap sized to accommodate the disposable cover without compressing the disposable cover between the first jaw and the cartridge body when the first jaw is in the closed position.

12. The surgical instrument of claim 7, wherein the cartridge body defines a groove, wherein the needle is positioned in the groove of the cartridge body, wherein the first jaw has a jaw groove complementing the groove of the cartridge body, wherein the needle is operable to orbit along the jaw groove and the groove of the cartridge body when the first jaw is in the closed position.

13. The surgical instrument of claim 7, wherein the suture cartridge further comprises a blocker element positioned adjacent to the needle, wherein blocker element is configured to engage the needle to prevent the needle from traveling in a first orbital direction while permitting the needle to travel in a second orbital direction.

14. The surgical instrument of claim 13, wherein the blocker element is resiliently mounted to the body and is configured to move between a blocked position and an unblocked position, wherein in the blocked position the blocker element is configured to engage the needle to inhibit the needle from traveling in the first orbital direction, and wherein in the unblocked position the blocker element is configured to permit the needle to travel in the second orbital direction.

15. The surgical instrument of claim 14, wherein the needle has a leading end portion and a trailing end portion, wherein the leading end portion is configured to urge the blocker element from the blocked position to the unblocked position while actuating in the second orbital direction, wherein the trailing end portion is configured to engage the blocker element and inhibit the needle from actuating in the first orbital direction.

16. A surgical instrument, comprising:
   (a) a shaft having a proximal end portion and a distal end portion;
   (b) a cartridge having a suturing needle; and
   (c) a cartridge receiving assembly projecting distally from the distal end portion of the shaft, the cartridge receiving assembly comprising:
   (i) a lower jaw, and
   (ii) an upper jaw,
   wherein the lower and upper jaws are configured to transition between an open configuration and a closed configuration, wherein the lower and upper jaws are configured to receive the cartridge therebetween when the lower and upper jaws are in the open configuration, wherein the lower and upper jaws are configured to secure the cartridge therebetween when the lower and upper jaws are in the closed configuration, wherein at least one of the lower jaw or the upper jaw is configured to receive the needle directly thereagainst and capture the needle between the lower and upper jaws along a circular path when the lower and upper jaws are in the closed configuration such that the at least one of the lower jaw or the upper jaw is configured to capture the needle within the cartridge while the needle orbits along the circular path between the lower and upper jaws.

17. A cartridge for a surgical suturing instrument having a user input member, the cartridge comprising:
(a) a cartridge body;
(b) a disposable cover removably connected to the cartridge body; and
(c) a needle positioned between the disposable cover and the cartridge body and contained in the cartridge body by the disposable cover such that the disposable cover secures the needle relative to the cartridge body while the disposable cover is removably connected to the cartridge body, wherein the disposable cover is removable from the cartridge body to release the needle relative to the cartridge body for being operatively actuated via the user input member to suture a tissue of a patient.

18. The cartridge of claim 17, wherein the disposable cover comprises a film, wherein the needle is positioned between the film and the cartridge body, wherein the film is removably adhered to the cartridge body for containing the needle in the cartridge body.

19. The cartridge of claim 18, wherein the disposable cover includes a grip tab extending from the film, wherein the grip tab is configured to be grasped by an operator for removing the film from the cartridge body.

20. The cartridge of claim 17, further comprising a blocker element positioned adjacent to the needle, and blocker element is configured to engage the needle to inhibit the needle from actuating in a reverse direction.

* * * * *